United States Patent
Graus et al.

(10) Patent No.: US 7,754,867 B2
(45) Date of Patent: Jul. 13, 2010

(54) NUCLEIC ACID MOLECULES ENCODING ANTI-P-SELECTIN ANTIBODIES

(75) Inventors: Yvo Graus, Odijk (NL); Jacques Himber, Guebwiller (FR); Miranda Jansen-Molenaar, Maarssen (NL); Dorothee Kling, Kandern-Tannenkirch (DE); Erhard Kopetzki, Penzberg (DE); Paul Parren, Odijk (NL); Frank Rebers, Utrecht (NL); Beat Steiner, Baettwil (CH); Anne Stern, Penzberg (DE); Pamela Strein, Neuried (DE); Kay-Gunnar Stubenrauch, Penzberg (CH); Jan van de Winkel, Zeist (NL); Martine van Vugt, Houten (NL)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/481,623

(22) Filed: Jun. 10, 2009

(65) Prior Publication Data

US 2009/0311779 A1   Dec. 17, 2009

Related U.S. Application Data

(62) Division of application No. 11/102,403, filed on Apr. 8, 2005, now Pat. No. 7,563,441.

(30) Foreign Application Priority Data

Apr. 13, 2004 (EP) .................................. 04008722

(51) Int. Cl.
*C12N 15/13* (2006.01)
*C12N 15/12* (2006.01)
*C12N 15/63* (2006.01)
*C12N 5/10* (2006.01)

(52) U.S. Cl. .................. 536/23.53; 536/23.1; 536/23.5; 435/252.3; 435/320.1; 435/326; 435/328; 435/332; 435/334; 435/343

(58) Field of Classification Search .................. None
See application file for complete search history.

(56) References Cited

U.S. PATENT DOCUMENTS

| 4,783,399 A | 11/1988 | Oldstone et al. |
| 5,800,815 A | 9/1998 | Chestnut et al. |
| 7,317,091 B2 | 1/2008 | Lazar et al. |
| 7,563,441 B2 * | 7/2009 | Graus et al. .............. 424/153.1 |
| 2006/0024298 A1 | 2/2006 | Lazar et al. |

FOREIGN PATENT DOCUMENTS

| WO | WO 93/06863 | 4/1993 |
| WO | WO 03/074679 | 9/1993 |
| WO | WO 93/21956 | 11/1993 |
| WO | WO 94/25067 | 11/1994 |
| WO | WO 94/29351 | 12/1994 |

OTHER PUBLICATIONS

Geng et al., J. Bio. Chem., 266, pp. 22323-22318 (1991).
European Journal of immunology, vol. 24, No. 10.01. (Oct. 1994) pp. 2542-2547, XP000567079.
Journal of Immunology, vol. 164, (2000), pp. 4178-4184, XP002965858.
Journal of Virology, vol. 75, No. 24, (Dec. 2001), pp. 12161-12168, XP002339184.
Reddy et al., Jour. of Immuno., 164, pp. 1925-1993 (2000).
Morgan A et al, *Immunology*, 86(2) 319-324 (1995).

* cited by examiner

*Primary Examiner*—Phillip Gambel
(74) *Attorney, Agent, or Firm*—George W. Johnston; Dennis P. Tramaloni; Brian C. Remy

(57) ABSTRACT

This invention relates to anti-P-selectin antibodies and, in particular, to anti-P-selectin antibodies and variants thereof that contain an Fc part derived from human origin and do not bind complement factor C1q. These antibodies have new and inventive properties causing a benefit for a patient suffering from critical limb ischemia or peripheral arterial occlusive disease (CLI/PAOD).

42 Claims, 9 Drawing Sheets

NUCLEIC ACID MOLECULES ENCODING ANTI-P-SELECTIN ANTIBODIES

PRIORITY TO RELATED APPLICATIONS

This application is a division of U.S. application Ser. No. 11/102,403, filed Apr. 8, 2005, now U.S. Pat. No. 7,563,441, which claims the benefit of European Application No. 04008722.3, filed Apr. 13, 2004. The entire contents of the above-identified applications are hereby incorporated by reference.

FIELD OF THE INVENTION

This invention relates generally to anti-P-selectin antibodies and, in particular, to anti-P-selectin antibodies that do not bind complement factor C1q. Preferably, these antibodies are human or humanized antibodies.

BACKGROUND OF THE INVENTION

P-selectin (CD62P, GMP-140, PADGEM, LECAM-3) is a 140 kDa calcium-dependent carbohydrate-binding protein that is expressed on the surfaces of activated platelets and endothelium in response to thrombin and other agonists (McEver et al., J Biol Chem 270:11025 (1995); Varki, Proc Natl Acad Sci USA 91:7390 (1994); Springer T A, Annu Rev Physiol 57:827 (1995)). In both cell types, P-selectin is stored in secretory granules, i.e. α-granules in platelets and Weibel-Palade bodies in endothelial cells (McEver et al., J Clin Invest 84:92 (1984)). It is a type I transmembrane glycoprotein which is composed of an $NH_2$-terminal lectin domain, followed by an EGF-like domain, nine short consensus repeats with homology to complement regulatory proteins, a transmembrane domain, and a short cytoplasmic tail (Johnston et al., Cell 56:1033 (1989)). The structure of P-selectin is similar to the other two members of the selectin family, E- and L-selectin, which are either expressed on cytokine-activated endothelial cells (E-selectin) or constitutively expressed on most classes of leukocytes (L-selectin).

All selectins are known to bind with low affinity to small sialylated, fucosylated oligosaccharides such as sialyl Lewis x ($sLe^x$; Foxall et al., J Cell Biol 117:895 (1992); Varki, Curr Opin Cell Biol 257:257 (1992)). P- and L-selectin, but not E-selectin, also bind to particular sulfated carbohydrates, such as heparin sulfate (for review, see McEver and Cummings, J Clin Invest 100:S97 (1997)). High affinity ligands for P-selectin are mucin-like glycoproteins (McEver et al., J Biol Chem 270:11025 (1995)), which consist of a polypeptide backbone with clusters of sialylated O-glycans. One sialomucin ligand to which P-selectin binds preferentially is P-selectin Glycoprotein ligand-1 (PSGL-1, CD162), which is normally expressed as a homodimer with two disulfide-linked subunits with relative molecular masses of approximately 120 kDa by circulating leukocytes. The binding site of P-selectin is localized to the extreme $NH_2$-terminal part of PSGL-1. Through its binding to its ligands, P-selectin mediates rolling of the leukocytes on activated platelets and endothelial cells. The rolling process effectively reduces the velocity of leukocyte movement, which is a prerequisite for firm adhesion and subsequent transmigration of leukocytes into the subendothelium but also for the accumulation of leukocytes in thrombi.

Studies using P-selectin deficient mice and P-selectin-specific blocking antibodies have shown that P-selectin participates in the pathophysiology of numerous acute and chronic inflammatory diseases including ischemia/reperfusion injury (Winn et al., J Clin Invest 92:2042 (1993); Massberg et al., Blood 92:507 (1998)). In addition, there is a clear contribution of P-selectin in cardiovascular diseases that have an inflammatory component such as atherosclerosis (Collins et al., J Exp Med 191: 189 (2000); Johnson et al., J Clin Invest 99:1037 (1997)), restenosis (Manka et al., Circulation 103: 1000 (2001); Bienvenu et al., Circulation 103:1128 (2001)) and thrombosis (Kumar et al., Circulation 99:1363 (1999); Andre et al., Proc Natl Acad Sci USA 97:13835 (2000); Blann et al., Br. J. Haematol 108:191 (2000); Myers et al., Thromb Haemostasis 85: 423 (2001). Evidently, inhibition of P-selectin function would be effective as a therapy in various diseases involving leukocyte adherence to vascular endothelium or platelets (see e.g. WO 93/06863).

Antibodies against P-selectin have been described in the state of the art and investigated for their anti-inflammatory and anti-thrombotic effects. U.S. Pat. No. 4,783,399 and WO 93/06863 describe mouse monoclonal antibodies against P-selectin reactive with activated platelets. Geng J. G. et al (J. Biol. Chem., 266 (1991) 22313-22318) describe mouse monoclonal antibodies binding to P-selectin amino acid (aa) fragment aa 60-75 (Cys to Glu, counting according to Swiss-Prot sequence P16109 which includes the signal sequence. WO 93/21956 refers to mouse monoclonal antibodies against P-selectin and humanized antibodies of IgG1 subclass competing with a defined antibody, binding in the presence of P-selectin fragment aa 60-75) and in the absence of calcium ions. None of the mentioned mouse monoclonal antibodies against human P-selectin is useful for the treatment of human patients. A humanized antibody against P-selectin of human IgG1 subclass mentioned in WO 93/21956 is in pre-clinical development.

SUMMARY OF THE INVENTION

The invention relates to antibodies characterized in that said antibodies bind P-selectin and do not bind human complement factor C1q. Preferably the antibodies do also not bind to human Fcγ receptor on NK cells. The antibodies according to the invention contain a Fc part derived from human origin. Preferably these antibodies are humanized or human antibodies. The antibodies have new and inventive properties causing a benefit for a patient suffering from inflammatory and thrombotic disorders, especially from peripheral arterial occlusive disease (PAOD) and critical limb ischemia (CLI).

BRIEF DESCRIPTION OF THE DRAWINGS

FIG. 3a: The anti-P-selectin antibodies do not affect the adhesion of thrombin-activated rat platelets to HL60 cells, whereas the commercially available polyclonal anti-P-selectin antibody (Pharmingen 09361A) inhibits this interaction. FIG. 3b: The antibodies of the invention inhibit the adhesion of activated cynomologus platelets to HL60 cells.

DETAILED DESCRIPTION OF THE INVENTION

Figure 1:
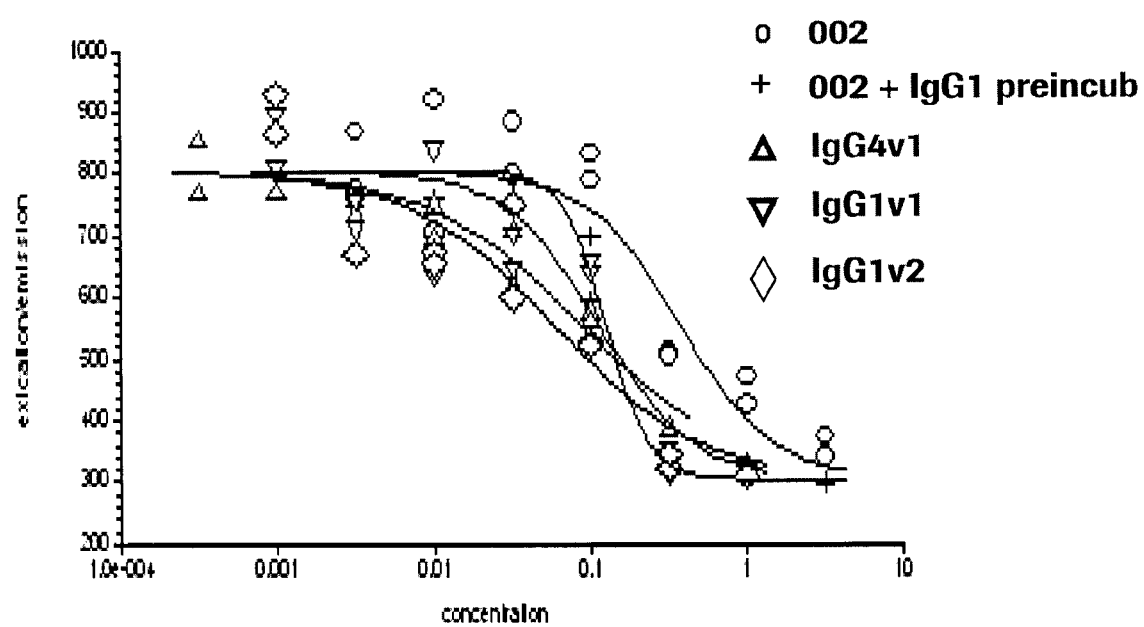
FIG. 1 shows that the antibodies of the invention inhibit the adhesion of leukocyte-like HL60 cells to purified P-selectin coated onto microtiter plates. The mutated antibodies are more potent than the non-mutated parent antibody.

The invention relates to antibodies characterized in that said antibodies bind P-selectin and do not bind human complement factor C1q. Preferably the antibodies do also not bind to human Fcγ receptor on NK cells. The antibodies according to the invention contain a Fc part derived from human origin. Preferably these antibodies are humanized or human antibodies. The antibodies have new and inventive properties causing a benefit for a patient suffering from inflammatory and thrombotic disorders, especially from peripheral arterial occlusive disease (PAOD) and critical limb ischemia (CLI).

Definitions

The term "P-selectin" refers to a 140 kDa protein expressed by human platelets and endothelial cells, as described by Hsu-Lin et al., J Biol Chem 259: 9121 (1984), and Mc Ever et al., J Clin Invest 84:92 (1989). This type I transmembrane glycoprotein is composed of an $NH_2$-terminal lectin domain, followed by an epidermal growth factor (EGF)-like domain and nine consensus repeat domains. It is anchored in the membrane by a single transmembrane domain and contains a small cytoplasmic tail. The present invention provides antibodies, which are capable of inhibiting one or more of the biological activities mediated by P-selectin, for example, its inflammatory or thrombotic activity. The antibodies bind to P-selectin and act by interfering with the binding of P-selectin to its ligand.

The term "P-selectin ligand" relates preferably to the high affinity and biologically relevant ligand of P-selectin such as the mucin-like glycoprotein P-selectin ligand glycoprotein-1 (PSGL-1), as described by Moore et al.; J Cell Biol 118:2445 (1992), Sako et al., Cell 75:1179 (1993) PSGL-1 is a type I membrane protein with an extracellular domain rich in serines, threonines, and prolines, including a series of decameric repeats linked with clusters of sialylated O-glycans. It is normally expressed as a homodimer with two disulfide-linked subunits with relative molecular masses of approximately 120 kDa by circulating leukocytes. The binding site of P-selectin is localized to the extreme $NH_2$-terminal part of PSGL-1. The sialomucin GPIbα which is expressed by platelets and has structural similarities with PSGL-1 was recently demonstrated to be a platelet ligand for P-selectin (Romo et al., J Exp Med 190:803 (1999). The physiological consequences of GPIbα binding to P-selectin are still under investigation, the interaction, however, is likely to contribute to the rolling and adherence of platelets to activated endothelial cells (Berndt et al., Thromb Haemost 86:178 (2001). P-selectin also binds with low affinity to small sialated, fucosylated oligosaccharides such as sialyl Lewis x (Foxall et al., J Cell Biol 117:895 (1992), Varki, Curr Opin Cell Biol 257 (1992) and to particular sulfated carbohydrates, such as heparin sulfate (McEver et al., J Biol Chem 270:11025 (1995).

The term "antibody" encompasses the various forms of antibodies, preferably monoclonal antibodies including but not being limited to whole antibodies, antibody fragments, human antibodies, humanized antibodies, chimeric antibodies and genetically engineered antibodies (variant or mutant antibodies) as long as the characteristic properties according to the invention are retained. Especially preferred are human or humanized monoclonal antibodies, especially as recombinant human antibodies.

The terms "monoclonal antibody" or "monoclonal antibody composition" as used herein refer to a preparation of antibody molecules of a single amino acid composition.

The term "chimeric antibody" refers to a monoclonal antibody comprising a variable region, i.e., binding region, from one source or species and at least a portion of a constant region derived from a different source or species, usually prepared by recombinant DNA techniques. Chimeric antibodies comprising a murine variable region and a human constant region are especially preferred. Such murine/human chimeric antibodies are the product of expressed immunoglobulin genes comprising DNA segments encoding murine immunoglobulin variable regions and DNA segments encoding human immunoglobulin constant regions. Other forms of "chimeric antibodies" encompassed by the present invention are those in which the constant region has been modified or changed from that of the original antibody to generate the properties according to the invention, especially in regard to C1q binding and/or Fc receptor (FcR) binding. Such "chimeric" antibodies are also referred to as "class-switched antibodies." Methods for producing chimeric antibodies involve conventional recombinant DNA and gene transfection techniques now well known in the art. See, e.g., Morrison, S. L., et al., Proc. Natl. Acad. Sci. USA 81 (1984) 6851-6855; U.S. Pat. Nos. 5,202,238 and 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See, e.g., Riechmann, L., et al., Nature 332 (1988) 323-327; and Neuberger, M. S., et al., Nature 314 (1985) 268-270. Particularly preferred CDRs correspond to those representing sequences recognizing the antigens noted above for chimeric and bifunctional antibodies. Other forms of "humanized antibodies" encompassed by the present invention are those in which the constant region has been modified or changed from that of the original antibody to generate the properties according to the invention, especially in regard to C1q binding and/or Fc receptor (FcR) binding.

The term "human antibody", as used herein, is intended to include antibodies having variable and constant regions derived from human germ line immunoglobulin sequences. Human antibodies are well-known in the state of the art (van Dijk and van de Winkel, Curr Opin Pharmacol 5:368 (2001). Human antibodies can also be produced in transgenic animals (e.g., mice) that are capable, upon immunization, of producing a full repertoire of human antibodies in the absence of endogenous immunoglobulin production. Transfer of the human germ-line immunoglobulin gene array in such germ-line mutant mice will result in the production of human antibodies upon antigen challenge (see, e.g., Jakobovits et al., Proc. Natl. Acad. Sci. USA, 90: 2551-2555 (1993); Jakobovits et al., Nature, 362:255-258 (1993); Bruggemann et al., Year in Immuno., 7:33 (1993)). Human antibodies can also be produced in phage display libraries (Hoogenboom and Winter, J. Mol. Biol., 227:381 (1992); Marks et al., J. Mol. Biol, 222:581 (19991)). The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)). As already mentioned for chimeric and humanized antibodies according to the invention the term "human antibody" as used herein also comprises such antibodies which are modified in the constant region to generate the properties according to the invention, especially in regard to C1q binding and/or FcR binding. In addition the invention comprises human antibodies which bind to C1q and/or FcR. Such human antibodies are characterized by a high selectivity for P-selectin vs. E- and L-selectin. Such antibodies according to the invention bind to P-selectin expressing cells with $EC_{50}$ values in the range of 0.01 and 0.07 µg/ml. $EC_{50}$ values on E-selectin and L-selectin expressing cells are preferably above 100 µg/ml. Such antibodies are preferable useful as intermediates for manufacturing human antibodies with the properties according to the invention.

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The "variable region" (variable region of a light chain (VL), variable region of a heavy chain (VH)) as used herein denotes each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions play a particularly important role in the binding specificity/affinity of the antibodies according to the invention and therefore provide a further object of the invention.

The terms "hypervariable region" or "antigen-binding portion of an antibody" when used herein refer to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. Especially, CDR3 of the heavy chain is the region which contributes most to antigen binding. CDR and FR regions are determined according to the standard definition of Kabat et al., Sequences of Proteins of Immunological Interest, 5th Ed. Public Health Service, National Institutes of Health, Bethesda, Md. (1991)) and/or those residues from a "hypervariable loop".

The term "nucleic acid or nucleic acid molecule", as used herein, is intended to include DNA molecules and RNA molecules. A nucleic acid molecule may be single-stranded or double-stranded, but preferably is double-stranded DNA.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

The "constant domains" are not involved directly in binding an antibody to an antigen, but exhibit various effector functions. Depending on the amino acid sequence of the constant region of their heavy chains, antibodies or immunoglobulins are divided in the classes: IgA, IgD, IgE, IgG and IgM, and several of these may be further divided into subclasses (isotypes), e.g. IgG1, IgG2, IgG3, and IgG4, IgA1 and IgA2. The heavy chain constant regions that correspond to the different classes of immunoglobulins are called α, δ, ε, γ and µ, respectively. The antibodies according to the invention are preferably of IgG type.

The Fc part of an antibody is directly involved in complement activation, C1q binding and Fc receptor binding. While the influence of an antibody on the complement system is dependent on certain conditions, binding to C1q is caused by defined binding sites in the Fc part. Such binding sites are known in the state of the art and described e.g. by Boakle et al., Nature 282 (1975) 742-743, Lukas et al., J. Immunol. 127 (1981) 2555-2560, Brunhouse and Cebra, Mol. Immunol. 16 (1979) 907-917, Burton et al., Nature 288 (1980) 338-344, Thommesen et al., Mol. Immunol. 37 (2000) 995-1004, Idusogie et al., J. Immunol. 164 (2000) 4178-4184, Hezareh et al., J. Virology 75 (2001) 12161-12168, Morgan et al., Imnunology 86 (1995) 319-324, EP 0307434. Such binding sites are e.g. L234, L235, D270, N297, E318, K320, K322, P331 and P329 (numbering according to EU index of Kabat, see below). Antibodies of subclass IgG1, IgG2 and IgG3 usually show complement activation and C1q and C3 binding, whereas IgG4 do not activate the complement system and do not bind C1q and C3. As used herein the term "Fc part derived from human origin" denotes a Fc part which is either a Fc part of a human antibody of the subclass IgG4 or a Fc part of a human antibody of the subclass IgG1, IgG2 or IgG3 which is modified in such a way that no C1q binding and/or FcR binding as defined below can be detected. A "Fc part of an antibody" is a term well known to the skilled artisan and defined on the basis of papain cleavage of antibodies. The antibodies according to the invention contain as Fc part a Fc part derived from human origin and preferably all other parts of the human constant regions. Preferably the Fc part is a human Fc part and especially preferred either from human IgG4 subclass or a mutated Fc part from human IgG1 subclass. Mostly preferred are the Fc parts and heavy chain constant regions shown in SEQ ID NO: 25-28 or of SEQ ID NO: 25 without PVA236 mutation.

Preferred Embodiments of the Invention

The invention comprises an antibody binding to P-selectin characterized in that the variable heavy chain amino acid sequence CDR3 of said antibody is selected from the group consisting of the heavy chain CDR3 sequences SEQ ID NO: 38, 39, 40, 41 or 42.

The invention preferably provides an antibody binding to P-selectin, comprising a variable heavy chain and a variable light chain, characterized in that the variable heavy chain comprises CDR sequences CDR1, CDR2 and CDR3 and CDR1 being selected from the group consisting of SEQ ID NOs: 29, 30, 31, 32, CDR2 being selected from the group consisting of SEQ ID NOs: 33, 34, 35, 36, 37, CDR3 being selected from the group consisting of SEQ ID NOs: 38, 39, 40, 41, 42, wherein said CDRs are selected independently of each other.

The antibody according to the invention is preferably characterized in that the variable light chain comprises CDR sequences CDR1, CDR2 and CDR3, and CDR1 is selected from SEQ ID NOs: 43, 44, CDR2 is selected from SEQ ID NOs: 45, 46 and CDR3 is selected from SEQ ID NOs: 47, 48, 49, 50, 51, 52 wherein said CDRs are selected independently of each other.

The antibody is preferably characterized in containing as heavy chain CDRs the CDRs of SEQ ID NO: 2 and as light chain CDRs the CDRs of SEQ ID NO: 1, as heavy chain CDRs the CDRs of SEQ ID NO: 4 and as light chain CDRs the CDRs of SEQ ID NO: 3, as heavy chain CDRs the CDRs of SEQ ID NO: 6 and as light chain CDRs the CDRs of SEQ ID NO: 5, as heavy chain CDRs the CDRs of SEQ ID NO: 8 and as light chain CDRs the CDRs of SEQ ID NO: 7, as heavy chain CDRs the CDRs of SEQ ID NO: 10 and as light chain CDRs the CDRs of SEQ ID NO: 9, as heavy chain CDRs the CDRs of SEQ ID NO: 12 and as light chain CDRs the CDRs of SEQ ID NO: 11, as heavy chain CDRs the CDRs of SEQ ID NO: 14 and as light chain CDRs the CDRs of SEQ ID NO: 13, as heavy chain CDRs the CDRs of SEQ ID NO: 16 and as light chain CDRs the CDRs of SEQ ID NO: 15, as heavy chain CDRs the CDRs of SEQ ID NO: 18 and as light chain CDRs the CDRs of SEQ ID NO: 17, as heavy chain CDRs the CDRs of SEQ ID NO: 20 and as light chain CDRs the CDRs of SEQ ID NO: 19, or as heavy chain CDRs the CDRs of SEQ ID NO: 22 and as light chain CDRs the CDRs of SEQ ID NO: 21.

The CDR sequences can be determined according to the standard definition of Kabat et al., Sequences of Proteins of Immunological Interest, 5th ed., Public Health Service, National Institutes of Health, Bethesda, Md. (1991). CDRs on each chain are separated by framework amino acids. CDRs of SEQ ID NO: 1-22 are shown in SEQ ID NO: 29-52.

The antibody according to the invention is preferably characterized in that said antibody binds P-selectin and comprises a variable heavy and light region independently selected from the group consisting of a) the heavy chain variable domain defined by amino acid sequence SEQ ID NO:2 and the light chain variable domain defined by SEQ ID NO:1;
b) the heavy chain variable domain defined by amino acid sequence SEQ ID NO:4 and the light chain variable domain defined by SEQ ID NO:3;
c) the heavy chain variable domain defined by amino acid sequence SEQ ID NO:6 and the light chain variable domain defined by SEQ ID NO:5;
d) the heavy chain variable domain defined by amino acid sequence SEQ ID NO:8 and the light chain variable domain defined by SEQ ID NO:7;
e) the heavy chain variable domain defined by amino acid sequence SEQ ID NO:10 and the light chain variable domain defined by SEQ ID NO:9;
f) the heavy chain variable domain defined by amino acid sequence SEQ ID NO:12 and the light chain variable domain defined by SEQ ID NO:11;
g) the heavy chain variable domain defined by amino acid sequence SEQ ID NO:14 and the light chain variable domain defined by SEQ ID NO:13;
h) the heavy chain variable domain defined by amino acid sequence SEQ ID NO:16 and the light chain variable domain defined by SEQ ID NO:15;
i) the heavy chain variable domain defined by amino acid sequence SEQ ID NO:18 and the light chain variable domain defined by SEQ ID NO:17;
j) the heavy chain variable domain defined by amino acid sequence SEQ ID NO:20 and the light chain variable domain defined by SEQ ID NO:19;
k) the heavy chain variable domain defined by amino acid sequence SEQ ID NO:22 and the light chain variable domain defined by SEQ ID NO:21.

The antibody according to the invention is preferably characterized in that the heavy chain variable region comprises an amino acid sequence independently selected from the group consisting of SEQ ID NO: 2, 4, 6, 8, 10, 12, 14, 16, 18, 20 and 22.

The antibody according to the invention is preferably characterized in that the light chain variable region comprises an amino acid sequence independently selected from the group consisting of SEQ ID NO: 1, 3, 5, 7, 9, 11, 13, 15, 17, 19 and 21.

The present invention refers to an antibody that binds P-selectin and does not bind complement factor C1q and/or Fc receptor. These antibodies do not elicit the complement dependent cytotoxicity (CDC) and/or antibody-dependent cellular cytotoxicity (ADCC). Preferably, this antibody is characterized in that it binds P-selectin, contains a Fc part derived from human origin and does not bind complement factor C1q. More preferably, this antibody is a human or humanized antibody.

The antibody according to the invention is preferably characterized in that the constant chains are of human origin. Such constant chains are well known in the state of the art and e.g. described by Kabat (see e.g. Johnson, G., and Wu, T. T., Nucleic Acids Res. 28 (2000) 214-218). For example a useful human heavy chain constant region comprises an amino acid sequence independently selected from the group consisting of SEQ ID NO: 24, 25, 26, 27 and 28. For example an useful human light chain constant region comprises an amino acid sequence of a kappa-light chain constant region of SEQ ID NO: 23.

The effector functions mediated by the Fc part of the antibody Fc region refer to effector functions that operate after the binding of an antibody to an antigen (these functions involve the activation of the complement cascade and/or cell activation by a Fc receptor (FcR)).

The function of the complement cascade can be assessed by the CH50 assay. Sheep red cells sensitized with anti-red cell antibodies (EA) are added to test serum to activate the classical pathway resulting in haemolysis. The volume of serum needed to lyse 50% of the red cells determines the CH50 unit. The AP-CH50 measures the alternative and the terminal pathways. The procedure is similar except that rabbit red cells are used. The alternative pathway is activated upon addition of test serum.

C1q and two serine proteases, C1r and C1s, form the complex C1, the first component of the complement dependent cytotoxicity (CDC) pathway. To activate the complement cascade C1 q binds to at least two molecules of IgG1 or one molecule of IgM, attached to the antigenic target (Ward and Ghetie, Therapeutic Immunology 2:77-94 (1995)). Burton described (Molec. Immunol., 22(3):161-206 (1985)) that the heavy chain region comprising amino acid residues 318 to 337 is being involved in complement fixation. Duncan and Winter (Nature 332:738-40 (1988)), using site directed mutagenesis, reported that Glu318, Lys320 and Lys322 form the binding site to C1q. The role of Glu318, Lys320 and Lys 322 residues in the binding of C1q was confirmed by the ability of a short synthetic peptide containing these residues to inhibit complement mediated lysis.

The term "complement-dependent cytotoxicity (CDC)" refers to lysis of P-selectin expressing human endothelial cells and platelets by the antibody according to the invention in the presence of complement. CDC is measured preferably by the treatment of P-selectin expressing human endothelial cells and platelets with an antibody according to the invention in the presence of complement. The cells are preferably labeled with calcein. CDC is found if the antibody induces lysis of 20% or more of the target cells at a concentration of 30 µg/ml. However, the inventors have found that for the properties of the antibodies according to the invention reduced binding to the complement factor C1q in an ELISA assay is essential. In such an assay in principle an ELISA plate is coated with concentration ranges of the antibody, to which purified human C1q or human serum is added. C1q binding is detected by an antibody directed against C1q followed by a peroxidase-labeled conjugate. Detection of binding (maximal binding Bmax) is measured as optical density at 405 nm (OD405) for peroxidase substrate ABTS (2,2'-Azino-di-[3-ethylbenzthiazoline-6-sulfonate (6)]. Accordingly the present invention refers to an antibody, characterized in that non-binding of the antibody to complement factor C1q refers to such an ELISA assay measurement wherein the maximal binding (Bmax) of C1q to the antibody at a concentration of 10 µg/ml of the antibody is ≦30% of Bmax of the antibody LC 1004-002 of cell line hu-Mab<P-selectin>LC 1004-002 (DSM ACC2641) preferably 20% or lower.

It is further preferred, that an antibody according to the invention shows a reduced binding to complement factor C3 in an ELISA assay. The assay is performed in the same manner as the C1q assay. In such an assay in principle an ELISA plate is coated with concentration ranges of the antibody, to which purified human C3 or human serum is added. C3 binding is detected by an antibody directed against C3 followed by a peroxidase-labeled conjugate. Detection of binding (maximal binding Bmax) is measured as optical density at 405 nm (OD405) for peroxidase substrate ABTS (2,2'-Azino-di-[3-ethylbenzthiazolinesulfonate (6)]. Accordingly the present invention refers to an antibody, characterized in that non-binding of the antibody to complement factor C3 refers to such an ELISA assay measurement wherein the maximal binding (Bmax) of C3 to the antibody at a concentration of 10 µg/ml of the antibody is 10% of Bmax of antibody LC 1004-002 of cell line hu-Mab<P-selectin>LC 1004-002 (DSM ACC2641)., preferably 5% or lower.

The term "antibody-dependent cellular cytotoxicity (ADCC)" is a function mediated by Fc receptor binding and refers to lysis of P-selectin expressing target cells by an antibody according to the invention in the presence of effector cells. ADCC is measured preferably by the treatment of a preparation of P-selectin expressing endothelial cells with an antibody according to the invention in the presence of effector cells such as freshly isolated PBMC (peripheral blood mononuclear cells) or purified effector cells from buffy coats, like monocytes or NK (natural killer) cells. Target cells are labeled with $^{51}$Cr and subsequently incubated with the antibodies. The labeled cells are incubated with effector cells and the supernatant is analyzed for released $^{51}$Cr. Controls include the incubation of the target endothelial cells with effector cells but without the antibody. The capacity of the antibodies to induce the initial steps mediating ADCC was determined by measuring their binding to Fcγ receptors expressing cells, such as granulocytes (expressing FcγRII and RIII), NK cells (expressing FeγRIII) and monocytes (expressing FcγRI and RII).

Fc receptor binding effector functions can be mediated by the interaction of the Fc region of an antibody with Fc receptors (FcRs), which are specialized cell surface receptors on hematopoietic cells. Fc receptors belong to the immunoglobulin superfamily, and have been shown to mediate both the removal of antibody-coated pathogens by phagocytosis of immune complexes, and the lysis of erythrocytes and various other cellular targets (e.g. tumor cells) coated with the corresponding antibody, via antibody dependent cell mediated cytotoxicity (ADCC). Van de Winkel and Anderson, J. Leuk. Biol. 49:511-24 (1991). FcRs are defined by their specificity for immunoglobulin isotypes; Fc receptors for IgG antibodies are referred to as FcγR, for IgE as FcεR, for IgA as FcαR and so on. Fc receptor binding is described e.g. in Ravetch and Kinet, Ann. Rev. Immunol. 9 (1991) 457-492, Capel et al., Immunomethods 4 (1994) 32-34, de Haas et al., J. Lab. Clin. Med. 126 (1995) 330-341 and Gessner et al., Ann. Hematol. 76 1998) 231-248. The antibodies according to the invention preferably show a reduced binding to Fcγ receptors, preferably to FγcRI, -IIA, -IIB, and/or IIIA.

The antibodies according to the present invention antibodies preferably do not elicit any effector function and do not bind to FcγR presented on NK cells. The term "no binding of FcγR" therefore means that in an antibody concentration of 10 µg/ml the binding of an antibody according to the invention to NK cells is 1% or less of the binding found for antibody LC 1004-002 of cell line hu-Mab<P-selectin>LC 1004-002 (DSM ACC2641).

While IgG4 shows reduced FcR binding, antibodies of other IgG subclasses show strong binding. However Pro238, Asp265, Asp270, Asn297 (loss of Fc carbohydrate), Pro329 and 234, 235, 236 and 237 Ile253, Ser254, Lys288, Thr307, Gln311, Asn434, and His435 are residues which provides if altered also reduced FcR binding (Shields et al. J. Biol. Chem. 276 (2001), 6591-6604, Lund et al. FASEB J. 9 (1995), 115-119, Morgan et al. Immunology 86 (1995) 319-324, EP 0307434). Preferably an antibody according to the invention is in regard to FcR binding of IgG4 subclass or of IgG1 or IgG2 subclass with a mutation in S228, L234, L235 and/or D265, and/or contains the PVA236 or GLPSS331 mutation.

Especially preferred are the mutations S228P (IgG4), L234A (IgG1), L235A (IgG1), L235E (IgG4), GLPSS331(IgG1) and/or PVA236 (IgG1). Preferred combinations of mutations are also shown in table 1. An additional preferred combination is D265A/N297A.

The term "binding to P-selectin" as used herein means the binding of the antibody to P-selectin in either a BIAcore® assay (Pharmacia Biosensor AB, Uppsala, Sweden) or in an ELISA in which either purified P-selectin or P-selectin CHO transfectants are coated onto microtiter plates.

In the BIAcore® assay the antibody is bound to a surface and binding of P-selectin is measured by Surface Plasmon Resonance (SPR). The affinity of the binding is defined by the terms ka (rate constant for the association of the antibody from the antibody/antigen complex), kd (dissociation constant), and $K_D$ (kd/ka). The antibodies according to the invention show a $K_D$ of $10^{-8}$ or less, preferably of about $10^{-11}$ to $10^{-9}$ M (see examples). Accordingly, the present invention refers to an antibody as described above, wherein the antibody binds to P-selectin with a $K_D$ value of less than $10^{-8}$ M in a BIAcore® assay, preferably wherein the $K_D$ range is $10^{-11}$ to $10^{-9}$ M.

Preferably, the antibody is of IgG1 or IgG4 human subtype. More preferably, the antibody is characterized in that the antibody is an antibody of human subclass IgG1, containing (comprising) at least one mutation in L234, L235, D270, N297, E318, K320, K322, P331 and/or P329 or an antibody of human subclass IgG4, containing (comprising) at least one mutation in L235 and S228 (numbering according to EU index).

In the P-selectin-specific ELISA purified P-selectin is coated onto microtiter plates and the binding of the antibody to P-selectin is detected with a biotinylated anti-human IgG and the usual steps of an ELISA. The $EC_{50}$ values in this assay range preferably between 0.002 and 0.03 µg/ml on P-selectin CHO cells, i.e. the present invention refers to antibodies, wherein the EC50 values for P-selectin binding are in the range of 0.002 to 0.03 µg/ml on P-selectin presenting CHO cells in an ELISA assay. In an assay in which P-selectin expressing CHO transfectants are coated onto the microtiter plate, the EC50 values range between 0.01 and 0.08 µg/ml, preferably between 0.01 and 0.04 µg/ml.

$EC_{50}$ values on E- and L-selectin transfectants are preferably above 100 µg/ml. The antibodies of the present invention are characterized in that they bind at least 1000 fold more specifically to P-selectin than to E- and/or L-selectin as measured by $EC_{50}$ values in an ELISA assay, wherein P- and E- and/or L-selectin are coated onto the microtiter plate.

The term "inhibiting the binding of the P-selectin ligand to P-selectin" as used herein refers to the binding of purified or cell-expressed P-selectin to its ligand presented on HL60 cells. The binding of P-selectin to its ligand is inhibited by the antibodies according to the invention. The inhibition is measured as $IC_{50}$ in in vitro assays analyzing the capacity of the antibody to inhibit binding of P-selectin to a ligand. Such assays are described in the Examples. They use as suitable sources of P-selectin affinity purified P-selectin and activated platelets and as suitable sources of the ligand leukocyte-like cells, such as HL60 cells. In such assays the adhesion of HL60 cells, expressing PSGL-1 as the physiologically relevant ligand of P-selectin, to P-selectin or activated platelets is measured without and with increasing concentrations of the antibody. The $IC_{50}$ values are measured as average values of at least three independent measurements. Inhibiting means an $IC_{50}$ value of no more than 1 µg/ml, preferably 0.5 to 0.08 µg/ml.

The antibodies of the present invention inhibit the adhesion of leukocyte-like HL60 cells to purified P-selectin with IC50 values in the range of 0.08 to 0.5 µg/ml, preferably 0.08 to −0.11 µg/ml. The adhesion of leukocyte-like HL60 cells to activated platelets is inhibited with IC50 values in the range of 0.05 to 0.3 µg/ml.

Accordingly, further embodiments of the present invention refer to antibodies, characterized in that the EC50 values for P-selectin binding is in the range of 0.01 to 0.08 µg/ml in an ELISA assay wherein P-selectin expressing CHO transfectants are coated onto the microtiter plate. The preferred range is 0.01 to 0.04 µg/ml. The EC50 values on E- and L-selectin transfectants are above 100 µg/ml. In a further embodiment the antibodies of the present invention inhibit the adhesion of leukocyte-like HL60 cells to purified P-selectin with IC50 values between 0.08 to 0.5 µg/ml. The preferred range is 0.08 to 0.11 µg/ml.

The antibodies of the present invention inhibit the interaction of leukocytes with a monolayer of platelets by preferably more than 70% in a fully human flow system (at a concentration of 10 µg/ml). In addition these antibodies inhibit the adhesion of leukocytes to activated endothelial cells in a human flow system in the range of 60-90% at a concentration of 3 µg/ml (with differential effects on leukocyte subtypes).

The antibodies of the present invention are preferably capable of binding to P-selectin in the presence of the P-selectin fragment aa 60-75 (Swiss-Prot sequence P16109) and/or do not competitively inhibit the binding of an antibody secreted by a cell line designated ATCC Accession No. HB11041 to P-selectin.

The antibodies of the invention preferably do not inhibit the interaction of P-selectin with platelet membrane glycoprotein GPIbα in an ELISA assay format. In the ELISA glycocalicin, the soluble extracellular portion of GPIbα was immobilized on the wells of microtiter plates, as described (Romo et al., J Exp Med 190:803 (1999), and the binding of purified P-selectin after preincubation with the P-selectin HuMabs was detected with a polyclonal anti-P-selectin antibody.

In a further preferred embodiment of the present invention, the antibody, characterized in that does not bind the C3 protein, more preferably it is characterized in that it does not elicit complement-dependent cytotoxicity (CDC). Further, the antibody may be characterized it does not bind to Fcγ receptors on NK effector cells. Preferably, the antibody is characterized that it is an antibody of human subclass IgG1, containing at least one mutation in L234, L235, D270, N297, E318, K320, K322, P331 and/or P329 or an antibody of human subclass IgG4, containing at least one mutation in L235 and S228 (numbering according to EU index). In a further preferred embodiment, the antibody is characterized in that it does not elicit antibody-dependent cellular cytotoxicity (ADCC).

In an even more preferred embodiment, the antibodies of the present invention are characterized in that they bind P-selectin and that they comprise a variable region independently selected from the group consisting of
a) the light chain variable domain defined by amino acid sequence SEQ ID NO:1 and the heavy chain variable domain defined by SEQ ID NO:2;
b) the light chain variable domain defined by amino acid sequence SEQ ID NO:3 and the heavy chain variable domain defined by SEQ ID NO:4;
c) the light chain variable domain defined by amino acid sequence SEQ ID NO:5 and the heavy chain variable domain defined by SEQ ID NO:6;

d) the light chain variable domain defined by amino acid sequence SEQ ID NO:7 and the heavy chain variable domain defined by SEQ ID NO:8;
e) the light chain variable domain defined by amino acid sequence SEQ ID NO:9 and the heavy chain variable domain defined by SEQ ID NO:10;
f) the light chain variable domain defined by amino acid sequence SEQ ID NO:11 and the heavy chain variable domain defined by SEQ ID NO:12;
g) the light chain variable domain defined by amino acid sequence SEQ ID NO:13 and the heavy chain variable domain defined by SEQ ID NO:14;
h) the light chain variable domain defined by amino acid sequence SEQ ID NO:15 and the heavy chain variable domain defined by SEQ ID NO:16;
i) the light chain variable domain defined by amino acid sequence SEQ ID NO:17 and the heavy chain variable domain defined by SEQ ID NO:18;
j) the light chain variable domain defined by amino acid sequence SEQ ID NO:19 and the heavy chain variable domain defined by SEQ ID NO:20; and
k) the light chain variable domain defined by amino acid sequence SEQ ID NO:21 and the heavy chain variable domain defined by SEQ ID NO:22.

Preferably, the antibodies comprise the light chain variable domain defined by amino acid sequence SEQ ID NO:3 and the heavy chain variable domain defined by SEQ ID NO:4.

The preferred antibodies are characterized in that the antibodies are of human IgG4 subclass or comprise at least one amino acid mutation causing non-binding to complement factor C1q. These variant antibodies comprise for example the amino acid sequence independently selected from the group consisting of SEQ ID NO: 25 or SEQ ID NO:26 and SEQ ID NO:28.

A "variant" anti-P-selectin antibody, refers herein to a molecule which differs in amino acid sequence from a "parent" anti-P-selectin antibody amino acid sequence by virtue of addition, deletion and/or substitution of one or more amino acid residue(s) in the parent antibody sequence. In the preferred embodiment, the variant comprises one or more amino acid substitution(s) in one or more constant or variable region(s) of the parent antibody, preferably in the constant region. For example, the variant may comprise at least one, e.g. from about one to about ten, and preferably from about two to about five, substitutions in one or more variable regions of the parent antibody. Ordinarily, the variant will have an amino acid sequence having at least 90% amino acid sequence identity with the parent antibody constant and/or variable domain sequences, more preferably at least 95%, and most preferably at least 99%.

Identity or homology with respect to this sequence is defined herein as the percentage of amino acid residues in the candidate sequence that are identical with the parent antibody residues, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind human P-selectin and preferably has properties, which are superior to those of the parent antibody. For example, the variant may have a stronger binding affinity, enhanced ability to treat a disease associated with critical limb ischemia or peripheral arterial occlusive disease (CLI/PAOD).

The variant antibody of particular interest herein is one which displays at least about 4 fold, enhancement in inhibitory activity in the adhesion assay when compared to the parent antibody because of the elimination of the binding to the Fcγ receptors.

The "parent" antibody herein is one, which is encoded by an amino acid sequence used for the preparation of the variant. Preferably, the parent antibody has a human framework region and, if present, has human antibody constant region(s). For example, the parent antibody may be a humanized or human antibody.

The antibodies according to the invention include, in addition, such antibodies having "conservative sequence modifications", nucleotide and amino acid sequence modifications, which do not affect or alter the above-mentioned characteristics of the antibody according to the invention. Modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-P-selectin antibody can be preferably replaced with another amino acid residue from the same side chain family.

Amino acid substitutions can be performed by mutagenesis based upon molecular modeling as described by Riechmann, L., et al., Nature 332 (1988) 323-327 and Queen, C., et al., Proc. Natl. Acad. Sci. USA 86 (1989) 10029-10033.

In a further preferred embodiment the antibodies comprise an κ-light chain constant region as defined by SEQ ID NO:23.

Preferred antibodies according to the invention are antibodies defined as IgG1v1 (PVA-236; GLPSS331 as specified by E233P; L234V; L235A; delta G236; A327G; A330S; P331S), IgG1v2 (L234A; L235A) and IgG4v1 (S228P; L235E).

In a further preferred embodiment, these antibodies also comprise antibody fragments selected from the group consisting of Fab, F(ab')$_2$ and single-chain fragments.

The invention further comprises a method for the production of an antibody according to the invention comprising the steps of a) transforming a host cell with a first nucleic acid sequence encoding a light chain of a parent human antibody according to the invention and a second DNA sequence encoding a heavy chain of said parent human antibody wherein the Fc part is modified in that said Fc part does not bind complement factor C1q and/or Fc receptor; b) expressing said first and second DNA sequence so that said antibody heavy and light chains are produced and c) recovering said antibody from the host cell or host cell culture.

The invention also refers to intermediate antibodies, i.e. anti-P-selectin antibodies characterized in that these antibodies are human or humanized antibodies and bind at least 1000 fold more specifically to P-selectin than to E- or L-selectin as measured in an ELISA assay wherein P- and E- and/or L-selectin are coated onto the microtiter plate. Preferably these antibodies are IgG1 or IgG4 antibodies. These antibodies may also comprise the amino acid sequence as defined by SEQ ID NO:24 γ1 heavy chain constant region or SEQ ID NO:27 γ4 heavy chain constant region. Especially, these antibodies refer to the antibodies produced by a cell line selected from the group consisting of hu-Mab<P-selectin>LC 1004-001 (DSM ACC2640), hu-Mab<P-selectin>LC 1004-002 (DSM ACC2641) and hu-Mab<P-selectin>LC 1004-017 (DSM ACC2642).

The antibodies according to the invention include, in addition, such antibodies having "conservative sequence modifications", nucleotide and amino acid sequence modifications, which do not affect or alter the above-mentioned characteristics of the antibody according to the invention. Modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted non-essential amino acid residue in a human anti-P-selectin antibody can be preferably replaced with another amino acid residue from the same side chain family.

Amino acid substitutions can be performed by mutagenesis based upon molecular modeling as described by Riechmann, L., et al., Nature 332 (1988) 323-327 and Queen, C., et al., Proc. Natl. Acad. Sci. USA 86 (1989) 10029-10033.

The invention further embodies an antibody (such as for example an antibody molecule) containing a Fc part derived from human origin wherein the antibody binds to P-selectin and is non-binding to complement factor C1q and wherein, in a further embodiment, said antibody is selected from the group consisting of a) human subclass IgG1 antibody comprising at least one mutation in L234, L235, D270, N297, E318, K320, K322, P331 and P329 and b) human subclass IgG4 antibody wherein S228 is replaced by P and L235 is replaced by E. In another further embodiment, the antibody is an anti-P-selectin antibody produced by a hybridoma cell line selected from the group consisting of DSM ACC2640, DSM ACC2641 and DSM ACC2642. The invention also discloses pharmaceutical compositions of the antibody of the invention, further comprising at least one pharmaceutically acceptable excipient.

The invention further comprises a method for the preparation of such an antibody according to the invention under conditions which allow synthesis and recovery of the antibody, as well as pharmaceutical compositions of the such produced antibody. The method of preparation may additionally comprise a nucleic acid molecule which encodes the antibody of the invention, a vector that comprises said nucleic acid molecule, and/or a host cell comprising said vector. The invention also comprises a kit for the detection of the presence of P-selectin protein comprising the said antibody of the invention as disclosed above and further alternatively comprises one or more of the group consisting of a nucleic acid molecule which encodes the said antibody of the invention, a vector that comprises said nucleic acid molecule, and/or a host cell comprising said vector.

The invention also further comprises a method for treatment of a patient in need of therapy comprising administering to the patient a therapeutically effective amount of the antibody of the invention. The invention further embodies a medicament comprising the antibody of the invention for use in such therapy administration and treatment and in particular for the treatment of inflammatory and thrombotic disorders, more particularly for the treatment of PAOD and CLI.

The present invention also comprises nucleic acid molecules encoding an antibody mentioned above, the corresponding vectors comprising these nucleic acids and the corresponding host cell for these vectors. The invention encompasses a method for the preparation of the antibodies comprising culturing the corresponding host cells under conditions that allow synthesis of said antibody molecules and recovering said antibodies from said culture, e.g. by expressing a nucleic acid encoding a heavy chain and a nucleic acid encoding a light chain in a prokaryotic or eukaryotic host cell and recovering said polypeptide from said cell Diagnostic and therapeutic uses for the antibody are contemplated. In one diagnostic application, the invention provides a method for determining the presence of the P-selectin protein comprising exposing a sample suspected of containing P-selectin to the anti-P-selectin antibody and determining binding of the antibody to the sample. For this use, the invention provides a kit comprising the antibody and instructions for using the antibody to detect the P-selectin protein.

The antibodies of the present invention are useful for treatment of inflammatory and thrombotic diseases. Such diseases include vascular disorders such as atherosclerosis, arterial and deep venous thrombosis, restenosis after angioplasty or stent placement. Preferred applications are peripheral arterial occlusive disease (PAOD) and critical limb ischemia (CLI). Other applications are the treatment of post-ischemic leukocyte-mediated tissue damage caused by myocardial infarction, cerebral ischemic event (e.g. stroke), renal infarction, and the like. The antibodies are also suitable for treatment of sepsis, acute leukocyte-mediated lung-injury, and allergic reactions such as asthma. Other applications are the prevention of organ transplant rejection and autoimmune diseases including rheumatoid arthritis. In addition, tumor metastasis can be prevented by inhibiting the adhesion of circulating cancer cells.

The invention further provides a method for treating a mammal suffering from the abovementioned inflammatory and thrombotic disorders, especially from PAOD and CLI (peripheral arterial occlusive disease or critical limb ischemia).

The invention further provides the use of the above antibodies for therapy, e.g. for the manufacture of medicaments for the treatment of these diseases.

The invention relates also to the use of the antibodies as defined above for the manufacture of a pharmaceutical composition and comprises a pharmaceutical composition containing an antibody according to the invention with a pharmaceutically effective amount, optionally together with a buffer and/or an adjuvant useful for the formulation of antibodies for pharmaceutical purposes.

The invention further provides pharmaceutical compositions comprising such antibodies in a pharmaceutically acceptable carrier. In one embodiment, the pharmaceutical composition may be included in an article of manufacture or kit.

The invention further provides hybridoma cell lines, which produce such antagonistic monoclonal antibodies, e.g. the parent antibodies, according to the invention.

The preferred hybridoma cell lines according to the invention, hu-Mab<P-selectin>LC 1004-001 (antibody HuMab 001) hu-Mab<P-selectin>LC 1004-002 (antibody HuMab 002) and hu-Mab<P-selectin>LC 1004-017 (antibody HuMab 017) were deposited, under the Budapest Treaty on the international recognition of the deposit of microorganisms for the purposes of patent procedure, with Deutsche Sammlung von Mikroorganismen und Zellkulturen GmbH (DSMZ), Germany:

| Cell line | Deposition No. | Date of Deposit |
|---|---|---|
| hu-Mab<P-selectin>LC 1004-001 | DSM ACC2640 | 30 Mar. 2004 |
| hu-Mab<P-selectin>LC 1004-002 | DSM ACC2641 | 30 Mar. 2004 |
| hu-Mab<P-selectin>LC 1004-017 | DSM ACC2642 | 30 Mar. 2004 |

The antibodies obtainable from said cell lines are preferred embodiments of the invention.

The antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression, nucleic acids encoding light and heavy chains or fragments thereof are inserted into expression vectors by standard methods. Expression is performed in appropriate prokaryotic or eukaryotic host cells like CHO cells, NS0 cells, SP2/0 cells, HEK293 cells, COS cells, yeast, or E. coli cells, and the antibody is recovered from the cells (supernatant or cells after lysis).

Recombinant production of antibodies is well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-161; Werner, R. G., Drug Res. 48 (1998) 870-880.

The antibodies may be present in whole cells, in a cell lysate, or in a partially purified or substantially pure form. Purification is performed in order to eliminate other cellular components or other contaminants, e.g. other cellular nucleic acids or proteins, by standard techniques, including alkaline/SDS treatment, column chromatography and others well known in the art. See Ausubel, F., et al., ed. Current Protocols in Molecular Biology, Greene Publishing and Wiley Interscience, New York (1987).

Expression in NS0 cells is described by, e.g., Barnes, L. M., et al., Cytotechnology 32 (2000) 109-123; and Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A preferred transient expression system (HEK 293) is described by Schlaeger, E.-J., and Christensen, K., in Cytotechnology 30 (1999) 71-83 and by Schlaeger, E.-J., in J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The monoclonal antibodies are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies are readily isolated and sequenced using conventional procedures. The hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

Amino acid sequence variants (or mutants) of a human P-selectin antibody are prepared by introducing appropriate nucleotide changes into the antibody DNA, or by nucleotide synthesis. Such modifications can be performed, however, only in a very limited range, e.g. as described above. For example, the modifications do not alter the abovementioned antibody characteristics such as the IgG isotype and epitope binding, but may improve the yield of the recombinant production, protein stability or facilitate the purification.

Any cysteine residue not involved in maintaining the proper conformation of the anti-P-selectin antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Another type of amino acid variant of the antibody alters the original glycosylation pattern of the antibody. By altering is meant deleting one or more carbohydrate moieties found in the antibody, and/or adding one or more glycosylation sites that are not present in the antibody. Glycosylation of antibodies is typically N-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites).

Nucleic acid molecules encoding amino acid sequence variants of anti-P-selectin antibodies are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of humanized anti-P-selectin antibody.

The invention also pertains to immunoconjugates comprising the antibody according to the invention conjugated to a cytotoxic agent such as a chemotherapeutic agent, toxin (e.g., an enzymatically active toxin of bacterial, fungal, plant or animal origin, or fragments thereof), a radioactive isotope (i.e., a radioconjugate) or a prodrug of an agent for the prophylaxis or treatment of inflammatory and thrombotic disorders, especially from PAOD and CLI. Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters; (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediatnine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta, E. S., et al., Science 238 (1987) 1098-1104). Carbon-14-labeled 1-isothiocyanatobenzyl-3-methyldiethylene triaminepentaacetic acid (MX-DTPA) is an exemplary chelating agent for conjugation of radionucleotide to the antibody. See WO 94/11026.

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330, and in Aplin, J. D., and Wriston, J. C. Jr., CRC Crit. Rev. Biochem. (1981) 259-306.

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr, H. T., and Bahl, O. P., Arch. Biochem. Biophys. 259 (1987) 52-57 and by Edge, A. S., et al. Anal. Biochem. 118 (1981) 131-137. Enzymatic cleavage of carbohydrate moieties on antibodies can be achieved by the use of a variety of endo- and exo-glycosidases as described by Thotakura, N. R., and Bahl, O. P., Meth. Enzymol. 138 (1987) 350-359.

Another type of covalent modification of the antibody comprises linking the antibody to one of a variety of nonproteinaceous polymers, eg., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

In yet another aspect, the invention provides isolated B-cells from a transgenic non-human animal, e.g. a transgenic mouse, which express the human anti-P-selectin antibodies (e.g. the parent antibodies produced by a cell line selected from the group consisting of hu-Mab<P-selectin>LC 1004-001 (DSM ACC2640), hu-Mab<P-selectin>LC 1004-002 (DSM ACC2641) and hu-Mab<P-selectin>LC 1004-017(DSM ACC2642) according to the invention. KM mice are suitable transchromosomal mice. The KM mouse contains a human heavy chain transchromosome and a human kappa light chain transgene. The endogenous mouse heavy and light chain genes also have been disrupted in the KM mice such that immunization of the mice leads to production of human immunoglobulins rather than mouse immunoglobulins. Construction of KM mice and their use to raise human immunoglobulins is described in detail in WO 02/43478.

Preferably, the isolated B cells are obtained from a transgenic non-human animal, e.g., a transgenic mouse, which has been immunized with a purified or recombinant form of P-selectin antigen and/or cells expressing P-selectin. Preferably, the transgenic non-human animal, e.g. a transgenic mouse, has a genome comprising a human heavy chain transgene and a human light chain transgene encoding all or a portion of an antibody of the invention. The isolated B-cells are then immortalized to provide a source (e.g. a hybridoma) of human anti-P-selectin antibodies. Accordingly, the present invention also provides a hybridoma capable of producing human monoclonal antibodies according to the invention. In one embodiment, the hybridoma includes a B cell obtained from a transgenic non-human animal, e.g., a transgenic mouse having a genome comprising a human heavy chain transgene and a human light chain transgene encoding all or a portion of an antibody of the invention, fused to an immortalized cell.

In a particular embodiment, the transgenic non-human animal is a transgenic mouse having a genome comprising a human heavy chain transgene and a human light chain transgene encoding all or a portion of an antibody of the invention. The transgenic non-human animal can be immunized with a purified or enriched preparation of P-selectin antigen and/or cells expressing P-selectin. Preferably, the transgenic non-human animal, e.g. the transgenic mouse, is capable of producing P-selectin isotypes of human monoclonal antibodies to P-selectin.

The human monoclonal antibodies according to the invention can be produced by immunizing a transgenic non-human animal, e.g. a transgenic mouse, having a genome comprising a human heavy chain transgene and a human light chain transgene encoding all or a portion of an antibody of the invention, with a purified or enriched preparation of P-selectin antigen and/or cells expressing P-selectin. B cells (e.g. splenic B cells) of the animal are then obtained and fused with myeloma cells to form immortal, hybridoma cells that secrete human monoclonal antibodies against P-selectin.

In a preferred embodiment, human monoclonal antibodies directed against P-selectin can be generated using transgenic mice carrying parts of the human immune system rather than the mouse system. These transgenic mice, referred to herein as "HuMab" mice, contain a human immunoglobulin gene miniloci that encodes unrearranged human immunoglobulin genes which include the heavy ($\mu$ and $\gamma$) and $\kappa$ light chain (constant region genes), together with targeted mutations that inactivate the endogenous $\mu$ and $\kappa$ chain loci (Lonberg, N., et al., Nature 368 (1994) 856-859). Accordingly, the mice exhibit reduced expression of mouse IgM or K, and in response to immunization, the introduced human heavy and light chain transgenes undergo class switching and somatic mutation to generate high affinity human IgG monoclonal antibodies (Lonberg, N., et al., Nature 368 (1994) 856-859; reviewed in Lonberg, N., Handbook of Experimental Pharmacology 113 (1994) 49-101; Lonberg, N., and Huszar, D., Intern. Rev. Immunol. 25 (1995) 65-93; and Harding, F., and Lonberg, N., Ann. N. Acad. Sci. 764 (1995) 536-546). The preparation of HuMab mice is described in Taylor, L., et al., Nucleic Acids Research 20 (1992) 6287-6295; Chen, J., et al., International Immunology 5 (1993) 647-656; Tuaillon, N., et al., Proc. Natl. Acad. Sci. USA 90 (1993) 3720-3724; Choi, T. K., et al., Nature Genetics 4 (1993) 117-123; Chen, J., et al., EMBO J. 12 (1993) 821-830; Tuaillon, N., et al., Immunol. 152 (1994) 2912-2920; Lonberg, N., et al., Nature 368 (1994) 856-859; Lonberg, N., Handbook of Experimental Pharmacology 113 (1994) 49-101; Taylor, L., et al., Int. Immunol. 6 (1994) 579-591; Lonberg, N., and Huszar, D., Intern. Rev. Immunol. 25 (1995) 65-93; Harding, F., and Lonberg, N., Ann. N. Acad. Sci. 764 (1995) 536-546; Fishwild, D. M., et al., Nat. Biotechnol. 14 (1996) 845-851, the contents of all of which are hereby incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; 5,545,807; 5,770,429; WO 98/24884; WO 94/25585; WO 93/1227; WO 92/22645; and WO 92/03918.

To generate fully human monoclonal antibodies to P-selectin, HuMab mice can be immunized with a purified or enriched preparation of P-selectin antigen and/or cells expressing P-selectin in accordance with the general method, as described by Lonberg, N., et al., Nature 368 (1994) 856-859; Fishwild, D. M., et al., Nat. Biotechnol. 14 (1996) 845-851 and WO 98/24884. Preferably, the mice will be 6-16 weeks of age upon the first immunization. For example, a purified or enriched preparation of soluble P-selectin antigen (e.g. purified from P-selectin-expressing cells) can be used to immunize the HuMab mice intraperitoneally. In the event that immunizations using a purified or enriched preparation of P-selectin antigen do not result in antibodies, mice can also be immunized with cells expressing P-selectin, e.g., a tumor cell line, to promote immune responses. Cumulative experience with various antigens has shown that the HuMab transgenic mice respond best when initially immunized intraperitoneally (i.p.) with antigen in complete Freund's adjuvant, followed by every other week i.p. immunizations (for example, up to a total of 6) with antigen in incomplete Freund's adjuvant. The immune response can be monitored over the course of the immunization protocol with plasma samples being obtained by retroorbital bleeds. The plasma can be screened by ELISA, and mice with sufficient titers of anti-P-selectin human immunoglobulin can be used for immortalization of corresponding B cells. Mice can be boosted intravenously with antigen 3 to 4 days before sacrifice and removal of the spleen and lymph nodes. It is expected that 2-3 fusions for each antigen may need to be performed. Several mice will be immunized for each antigen. For example, a total of twelve HuMab mice of the HCo7 and HCo12 strains can be immunized.

The HCo7 mice have a JKD disruption in their endogenous light chain (kappa) genes (as described in Chen, J., et al., EMBO J. 12 (1993) 821-830), a CMD disruption in their endogenous heavy chain genes (as described in Example 1 of WO 01/14424), a KCo5 human kappa light chain transgene (as described in Fishwild, D. M., et al., Nat. Biotechnol. 14 (1996) 845-851), and a HCo7 human heavy chain transgene (as described in U.S. Pat. No. 5,770,429).

The HCo12 mice have a JKD disruption in their endogenous light chain (kappa) genes (as described in Chen, J., et al., EMBO J. 12 (1993) 821-830), a CMD disruption in their endogenous heavy chain genes (as described in Example 1 of WO 01/14424), a KCo5 human kappa light chain transgene (as described in Fishwild, D. M., et al., Nat. Biotechnol. 14 (1996) 845-851), and a HCo12 human heavy chain transgene (as described in Example 2 of WO 01/14424). The mouse lymphocytes can be isolated and fused with a mouse myeloma cell line using PEG based on standard protocols to generate hybridomas. The resulting hybridomas are then screened for the production of antigen-specific antibodies. For example, single cell suspensions of splenic and lymph node-derived lymphocytes from immunized mice are fused to one-sixth the number of SP 2/0 nonsecreting mouse myeloma cells (ATCC, CRL 1581) with 50% PEG. Cells are plated at approximately $2 \times 10^5$ in flat bottom microtiter plate, followed by about two weeks incubation in selective medium.

Individual wells are then screened by ELISA for human anti-P-selectin monoclonal IgM and IgG antibodies. Once extensive hybridoma growth occurs, medium is analyzed, usually after 10-14 days. The antibody secreting hybridomas are replated, screened again, and if still positive for human IgG, anti-P-selectin monoclonal antibodies, can be subcloned at least twice by limiting dilution. The stable subclones are then cultured in vitro to produce antibody in tissue culture medium for characterization.

Because CDR sequences are responsible for antibody-antigen interactions, it is possible to express recombinant antibodies according to the invention by constructing expression vectors that include the CDR sequences according to the invention onto framework sequences from a different human antibody (see, e.g., Riechmann, L., et al., Nature 332 (1998) 323-327; Jones, P., et al., Nature 321 (1986) 522-525; and Queen, C., et al., Proc. Natl. Acad. See. U.S.A. 86 (1989) 10029-10033). Such framework sequences can be obtained from public DNA databases that include germline human antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody at individual evenly across the variable region.

The invention further comprises the use of an antibody according to the invention for the diagnosis of P-selectin in vitro, preferably by an immunological assay determining the binding between P-selectin of a sample and the antibody according to the invention.

In another aspect, the present invention provides a composition, e.g. a pharmaceutical composition, containing one or a combination of human monoclonal antibodies, or the antigen-binding portion thereof, of the present invention, formulated together with a pharmaceutically acceptable carrier. More specifically, the composition is a pharmaceutical or a diagnostic composition and even more specifically the pharmaceutical composition comprises an antibody as defined above and at least one pharmaceutically acceptable excipient.

Pharmaceutical compositions of the invention also can be administered in combination therapy, i.e., combined with other agents. For example, the combination therapy can include a composition of the present invention with at least one agent useful in the prophylaxis or treatment a disease associated with critical limb ischemia (CLI/PAOD) or other conventional therapy.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A "pharmaceutically acceptable salt" refers to a salt that retains the desired biological activity of the antibody and does not impart any undesired toxicological effects (see e.g. Berge, S. M., et al., J. Pharm. Sci. 66 (1977) 1-19). Such salts are included in the invention. Examples of such salts include acid addition salts and base addition salts. Acid addition salts include those derived from nontoxic inorganic acids, such as hydrochloric salts.

A composition of the present invention can be administered by a variety of methods known in the art. As will be appreciated by the skilled artisan, the route and/or mode of administration will vary depending upon the desired results.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions.

Pharmaceutically acceptable excipients or carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

These compositions may also contain excipients or adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A typical weekly dosage might range from about 0.1 mg/kg to about 20 mg/kg or more, depending on the factors mentioned above.

The composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

The invention comprises a method for the treatment of a patient in need of therapy, characterized by administering to the patient a therapeutically effective amount of an antibody which binds P-selectin, contains a Fc part derived from human origin and does not bind complement factor C1q.

The invention comprises the use of an antibody which binds P-selectin, contains a Fc part derived from human origin and does not bind complement factor C1q for therapy.

The invention comprises the use of an antibody which binds P-selectin, contains a Fc part derived from human origin and does not bind complement factor C1q for the preparation of a medicament for the prophylaxis and treatment of inflammatory and thrombotic disorders.

The invention comprises the use of an antibody which binds P-selectin, contains a Fc part derived from human origin and does not bind complement factor C1q for the treatment of PAOD and CLI.

The present invention thus provides an antibody binding to P-selectin, not binding to complement factor C1q, containing an Fc part derived from human origin, and being characterized in that said antibody is an antibody of human subclass IgG1, containing at least one mutation in L234, L235, D270, N297, E318, K320, K322, P331 and/or P329 or is an antibody of human subclass IgG4 wherein S228 is replaced by P and L235 is replaced by E. In one embodiment the antibody is a human antibody. In another embodiment the antibody is a humanized antibody.

In one embodiment the present invention provides an antibody binding to P-selectin, not binding to complement factor C1q, containing an Fe part derived from human origin, and being characterized in that said antibody is an antibody of human subclass IgG1, containing at least one mutation in L234, L235, D270, N297, E318, K320, K322, P331 and/or P329 or is an antibody of human subclass IgG4 wherein S228 is replaced by P and L235 is replaced by E, wherein non-binding of the antibody to complement factor C1q refers to an ELISA assay measurement wherein the maximal binding (Bmax) of C1q to the antibody at a concentration of 10 µg/ml of the antibody is ≦30% of Bmax of the antibody LC 1004-002 of cell line hu-Mab<P-selectin>LC 1004-002 (DSM ACC2641). In another embodiment the maximal binding is ≦20% of Bmax of the antibody LC 1004-002 of cell line hu-Mab<P-selectin>LC 1004-002 (DSM ACC2641).

In one embodiment the present invention provides an antibody binding to P-selectin, not binding to complement factor C1q, containing an Fc part derived from human origin, and being characterized in that said antibody is an antibody of human subclass IgG1, containing at least one mutation in L234, L235, D270, N297, E318, K320, K322, P331 and/or P329 or is an antibody of human subclass IgG4 wherein S228 is replaced by P and L235 is replaced by E, wherein the antibody binds to P-selectin with a $K_D$ value of less than $10^{-8}$ M in a BIAcore assay. In another embodiment the $K_D$ range is $10^{-11}$ to $10^{-9}$ M.

In one embodiment the present invention provides an antibody binding to P-selectin, not binding to complement factor C1q, containing an Fc part derived from human origin, and being characterized in that said antibody is an antibody of human subclass IgG1, containing at least one mutation in L234, L235, D270, N297, E318, K320, K322, P331 and/or P329 or is an antibody of human subclass IgG4 wherein S228 is replaced by P and L235 is replaced by E, wherein the antibody binds at least 1000 fold more specifically to P-selectin than to E- and/or L-selectin as measured by EC50 values in an ELISA assay, wherein P- and E- and/or L-selectin are coated onto the microtiter plate. In another embodiment the EC50 values on E- and L-selectin transfectants are above 100 µg/ml.

In one embodiment the present invention provides an antibody binding to P-selectin, not binding to complement factor C1q, containing an Fc part derived from human origin, and being characterized in that said antibody is an antibody of human subclass IgG1, containing at least one mutation in L234, L235, D270, N297, E318, K320, K322, P331 and/or P329 or is an antibody of human subclass IgG4 wherein S228 is replaced by P and L235 is replaced by E, wherein the antibody inhibits the adhesion of leukocyte-like HL60 cells to purified P-selectin with an IC50 value of no more than 1 µg/ml. In another embodiment the IC50 value is in the range of 0.08 to 0.5 µg/ml. In still another embodiment the IC50 value is in the range of 0.08 to 0.11 µg/ml.

In one embodiment the present invention provides an antibody binding to P-selectin, not binding to complement factor C1q, containing an Fc part derived from human origin, and being characterized in that said antibody is an antibody of human subclass IgG1, containing at least one mutation in L234, L235, D270, N297, E318, K320, K322, P331 and/or P329 or is an antibody of human subclass IgG4 wherein S228 is replaced by P and L235 is replaced by E, wherein (a) the adhesion of leukocyte-like HL60 cells to activated platelets is inhibited with an IC50 value of 0.05 to 0.3 µg/ml;

(b) the antibody inhibits the interaction of leukocytes with a monolayer of platelets by more than 70%;

(c) the antibody inhibits the adhesion of leukocytes to activated endothelial cells in a human flow system in the range of 60 to 90% at a concentration of 3 µg/ml;

(d) the antibody does not bind the C3 protein;

(e) the antibody does not elicit complement-dependent cytotoxicity (CDC);

(f) the antibody does not bind to Fcγ receptors on NK effector cells; or (g) the antibody does not elicit antibody-dependent cellular cytotoxicity (ADCC).

In one embodiment the present invention provides an antibody binding to P-selectin characterized in that the variable heavy chain amino acid sequence CDR3 of said antibody is selected from the group consisting of the heavy chain CDR3 sequences SEQ ID NO: 38, 39, 40, 41 or 42.

In one embodiment the present invention provides an antibody binding to P-selectin, comprising a variable heavy chain and a variable light chain, characterized in that the variable heavy chain comprises CDR sequences CDR1, CDR2 and CDR3 and CDR1 being selected from the group consisting of SEQ ID NOs: 29, 30, 31, 32, CDR2 being selected from the group consisting of SEQ ID NOs: 33, 34, 35, 36, 37, CDR3 being selected from the group consisting of SEQ ID NOs: 38, 39, 40, 41, 42, wherein said CDRs are selected independently of each other.

In one embodiment the present invention provides an antibody characterized in that the variable light chain comprises CDR sequences CDR1, CDR2 and CDR3, and CDR1 is selected from SEQ ID NOs: 43, 44, CDR2 is selected from SEQ ID NOs: 45, 46 and CDR3 is selected from SEQ ID NOs: 47, 48, 49, 50, 51, 52 wherein said CDRs are selected independently of each other.

In one embodiment the present invention provides an antibody, characterized in that said antibody binds P-selectin and that the antibody comprises a variable region independently selected from the group consisting of a) the light chain variable domain defined by amino acid sequence SEQ ID NO:1 and the heavy chain variable domain defined by SEQ ID NO:2;

b) the light chain variable domain defined by amino acid sequence SEQ ID NO:3 and the heavy chain variable domain defined by SEQ ID NO:4;

c) the light chain variable domain defined by amino acid sequence SEQ ID NO:5 and the heavy chain variable domain defined by SEQ ID NO:6;

d) the light chain variable domain defined by amino acid sequence SEQ ID NO:7 and the heavy chain variable domain defined by SEQ ID NO:8;

e) the light chain variable domain defined by amino acid sequence SEQ ID NO:9 and the heavy chain variable domain defined by SEQ ID NO:10;

f) the light chain variable domain defined by amino acid sequence SEQ ID NO:11 and the heavy chain variable domain defined by SEQ ID NO:12;

g) the light chain variable domain defined by amino acid sequence SEQ ID NO:13 and the heavy chain variable domain defined by SEQ ID NO:14;

h) the light chain variable domain defined by amino acid sequence SEQ ID NO:15 and the heavy chain variable domain defined by SEQ ID NO:16;

i) the light chain variable domain defined by amino acid sequence SEQ ID NO:17 and the heavy chain variable domain defined by SEQ ID NO:18;

j) the light chain variable domain defined by amino acid sequence SEQ ID NO:19 and the heavy chain variable domain defined by SEQ ID NO:20; and k) the light chain variable domain defined by amino acid sequence SEQ ID NO:21 and the heavy chain variable domain defined by SEQ ID NO:22.

In one embodiment the present invention provides an antibody binding to P-selectin, not binding to complement factor C1q, containing an Fc part derived from human origin, and being characterized in that said antibody is an antibody of human subclass IgG1, containing at least one mutation in L234, L235, D270, N297, E318, K320, K322, P331 and/or P329 or is an antibody of human subclass IgG4 wherein S228 is replaced by P and L235 is replaced by E, wherein the antibody comprises the CDR1, CDR2 and CDR3 regions of the light chain variable domain defined by amino acid sequence SEQ ID NO:3 and the CDR1, CDR2 and CDR3 regions of the heavy chain variable domain defined by SEQ ID NO:4. In another embodiment the antibody comprises the light chain variable domain defined by amino acid sequence SEQ ID NO:3 and the heavy chain variable domain defined by SEQ ID NO:4.

In one embodiment the present invention provides an antibody binding to P-selectin, not binding to complement factor C1q, containing an Fc part derived from human origin, and being characterized in that said antibody is an antibody of human subclass IgG1, containing at least one mutation in L234, L235, D270, N297, E318, K320, K322, P331 and/or P329 or is an antibody of human subclass IgG4 wherein S228 is replaced by P and L235 is replaced by E, wherein (a) the antibody comprises at least one amino acid mutation in the Fc part causing non-binding to complement factor C1q;

(b) the human heavy chain constant region comprises the amino acid sequence independently selected from the group consisting of SEQ ID NO: 25, SEQ ID NO:26 and 28;

(c) the antibody comprises a κ-light chain constant region as defined by SEQ ID NO:23;

(d) the antibody comprises at least one amino acid mutation causing non-binding to complement C1q;

(e) the antibody comprises a heavy chain constant region selected from the group consisting of IgG1v1, IgG1v2 and IgG4v1; or (f) the antibody is a Fab, F(ab')$_2$ or a single-chain fragment.

In one embodiment the present invention provides an anti-P selectin antibody, characterized in that it a) is a human or humanized antibody, and b) binds at least 1000 fold more specifically to P-selectin than to E- or L-selectin as measured by EC50 values in an ELISA assay, wherein P- and E- and/or L-selectin are coated onto the microtiter plate. In another embodiment the antibody comprises the amino acid sequence as defined by SEQ ID NO:24, 25 or 26 γ1 heavy chain constant region or SEQ ID NO:27 or 28 γ4 heavy chain constant region. In still another embodiment the antibody is produced by a cell line selected from the group consisting of hu-Mab<P-selectin>LC 1004-001 (DSM ACC2640), hu-Mab<P-selectin>LC 1004-002 (DSM ACC2641) and hu-+Mab<P-selectin>LC 1004-017(DSM ACC2642).

It is to be understood that the invention provides the embodiments with the definitions as described in paragraphs above-.

The following examples, references, sequence listing and figures are provided to aid the understanding of the present invention, the true scope of which is set forth in the appended claims. It is understood that modifications can be made in the procedures set forth without departing from the spirit of the invention.

Description of the sequence listing

SEQ ID NO:1 LC1004-001 light chain, variable domain of HuMab 1004-001
SEQ ID NO:2 LC1004-001 heavy chain, variable domain of HuMab 1004-001
SEQ ID NO:3 LC1004-002 light chain, variable domain of HuMab 002
SEQ ID NO:4 LC1004-002 heavy chain, variable domain of HuMab 002
SEQ ID NO:5 LC1004-003 light chain, variable domain of HuMab 003
SEQ ID NO:6 LC1004-003 heavy chain, variable domain of HuMab 003
SEQ ID NO:7 LC1004-004 light chain (I), variable domain of HuMab 004 (I)
SEQ ID NO:8 LC1004-004 heavy chain (I), variable domain of HuMab 004 (I)
SEQ ID NO:9 LC1004-004 light chain (II), variable domain of HuMab 004 (II)
SEQ ID NO:10 LC1004-004 heavy chain (II), variable domain of HuMab 004 (II)
SEQ ID NO:11 Light chain, variable domain of HuMab 005
SEQ ID NO:12 Heavy chain, variable domain of HuMab 005
SEQ ID NO:13 Light chain, variable domain of HuMab 010 (I)
SEQ ID NO:14 Heavy chain, variable domain of HuMab 010 (I)
SEQ ID NO:15 Light chain, variable domain of HuMab 010 (II)
SEQ ID NO:16 Heavy chain, variable domain of HuMab 010 (II)
SEQ ID NO:17 Light chain, variable domain of HuMab 010 (III)
SEQ ID NO:18 Heavy chain, variable domain of HuMab 010 (III)
SEQ ID NO:19 Light chain, variable domain of HuMab 011
SEQ ID NO:20 Heavy chain, variable domain of HuMab 011
SEQ ID NO:21 Light chain, variable domain of HuMab 017
SEQ ID NO:22 Heavy chain, variable domain of HuMab 017
SEQ ID NO:23 κ light chain constant region
SEQ ID NO:24 γ1 heavy chain constant region
SEQ ID NO:25 γ1 heavy chain constant region PVA236/GLPSS331 (IgG1v1)
SEQ ID NO:26 γ1 heavy chain constant region L234A/L235A (IgG1v2)
SEQ ID NO:27 γ4 heavy chain constant region
SEQ ID NO:28 γ4 heavy chain constant region S228/L235E (IgG4v)
SEQ ID NO:29 -32 Heavy chain CDR1
SEQ ID NO:33 -37 Heavy chain CDR2
SEQ ID NO:38 -42 Heavy chain CDR3
SEQ ID NO:43 -44 Light chain CDR1
SEQ ID NO:45 -46 Light chain CDR2
SEQ ID NO:47 -52 Light chain CDR3
SEQ ID NO:53 -57 Various sequences of four or more amino acids as described herein.

Abbreviations:

Amino acids are abbreviated either in the three (Leu) or one letter code (L) Antibody HuMab 00X is also named antibody 00X. L234 means amino acid leucine at position 234 according to EU numbering (Kabat). L234A means amino acid leucine at position 234 is changed to alanine. PVA236 means that in the 236 region ELLG (SEQ ID NO: 53) of IgG1 or EFLG (SEQ ID NO: 56) of IgG4 is amended to PVA. GLPSS331 means that in the 331 region ALPAP (SEQ ID NO: 54) of IgG1 or GLPAP (SEQ ID NO: 57) of IgG2 is changed to GLPSS (SEQ ID NO: 55). Amendments in the other IgG subclasses are analogous.

EXAMPLES

Generation of a Hybridoma Cell Line Producing Anti-P-selectin Antibodies

Culture of Hybridomas

HuMab hybridomas were cultured in IMDM (Cambrex), Fetal clone 1 Bovine serum (Perbio Science), origin Hybridoma cloning factor (Igen), sodium pyruvate, penicillin/streptomycin, 2-mercaptoethanol, HAT (Sigma-Aldrich) and Kanamycin (Invitrogen) in 37° C. and 5% $CO_2$.

Generation of a Hybridoma Cell Line Producing Anti-P-selectin Antibodies

Immunization Procedure of Transgenic Mice

Protocol A:

10 HCo7 transgenic mice (5 males and 5 females), strain GG2201 (Medarex, San José, Calif., USA) were immunized with a recombinant truncated form of P-selectin which lacks the transmembrane and cytoplasmic domain of P-selectin and which was purchased from R&D Systems. For the first immunization 50 μg recombinant P-selectin, dissolved in 100 μl PBS, was mixed with 100 μl complete Freunds' adjuvant. For the remaining immunizations recombinant P-selectin coupled to KLH was used. For the second immunization 50 μg KLH-coupled recombinant P-selectin was dissolved in 100 μl PBS and mixed with 100 μl incomplete Freunds' adjuvant. For the remaining immunizations 20 μg KLH-coupled recombinant P-selectin was dissolved in 100 μl PBS and mixed with 100 μl incomplete Freunds' adjuvant. Immunizations were administered alternating interperitoneal and subcutaneous starting with an interperitoneal immunization.

Protocol B:

3 HCo7 (all female) and 3 KM (all male) transgenic mice, strain GG2489 (Medarex, San José, Calif., USA) were immunized with full-length P-selectin purified from human outdated platelets by immunoaffinity chromatography (s. below). For the first immunization, 50 µg of the purified P-selectin, dissolved in 100 µl PBS, was mixed with 100 µl complete Freunds' adjuvant (CFA; Difco Laboratories, Detroit, USA). For the second immunization, 50 µg of the purified P-selectin, dissolved in 100 µl PBS, was mixed with 100 µl incomplete Freunds' adjuvant (ICFA; Difco).

For all other immunizations, 20 µg of the purified P-selectin was used and mixed with 100 µl incomplete Freunds' adjuvant.

Antigen Specific ELISA

Anti-P-selectin titers in sera of immunized mice were determined by antigen specific ELISA. Plate (96 flat bottom ELISA plate, Greiner) was coated with 0.1 µg/ml purified P-selectin dissolved in PBS and coated overnight at room temperature. Thereafter, wells were blocked with PBSTC (PBS containing 0.05% Tween 20 (Sigma-Aldrich Chemie BV) and 2% chickenserum (Gibco)) for 1 hour at room temperature.

Tested serum taps were diluted 1:100 in PBSTC and added to the wells. Serum obtained from mice prior to immunization was dissolved 1:100 in PBSTC and used as negative control. A mouse antibody directed against human P-selectin (1/7, produced in house by Roche Basel) was dissolved 1:100 in PBSTC and used as a positive control. Plates were incubated for 1 hour at room temperature. Subsequently, plates were washed twice using PBST (PBS containing 0.05% Tween 20. Gt-α-huIgG-HRP (Jackson) was diluted 1:5000 in PBSTC and added to the wells containing the tested taps and the negative control. Rb-α-mIgG (Jackson) was diluted 1:3000 in PBSTC and added to the wells containing the positive control. Plates were incubated for 1 hour at room temperature. Finally, plates were washed twice using PBST and developed with freshly prepared ABTS® solution (1 mg/ml) (ABTS: 2,2'-azino bis(3-ethylbenzthiazoline-6-sulfonic acid) for 30 minutes at room temperature (RT) in the dark. Absorbance was measured at 405 nm.

Boosting of Mice

When serum titers of anti-P-selectin were sufficient, mice were additionally boosted twice with 20 µg recombinant human P-selectin in 100 µl PBS, intraveneously 4 and 3 days before fusion.

Hybridoma Generation

Mice were sacrificed and the spleen and lymph nodes flanking the abdominal aorta and vena cava were collected. Fusion of splenocytes and lymph node cells with the fusion partner SP 2.0 cells was performed according to standard operating procedures.

Human monoclonal antibodies with variable heavy and light sequences of SEQ ID NOs 1-22 were obtained by the immunization procedure.

κ-ELISA

To determine whether hybridomas that resulted from the fusion generate human antibodies, a κ-ELISA was performed. ELISA plates were coated with rat anti-human IgG κ-light chain antibody (DAKO) diluted 1/10000 in PBS by overnight incubation at 4° C. After discarding the wells, plates were blocked by incubation with PBSTC for 1 hour at room temperature. Thereafter, wells were incubated with hybridoma culture supernatant, 1/2 diluted in PBSTC. Culture medium 1/2 diluted in PBSTC was used as negative control, κ-light positive mouse serum 1/100 diluted in PBSTC served as positive control. Subsequently, wells were washed thrice and were incubated with HRP-conjugated rat anti-human IgG F(ab')$_2$ (DAKO), diluted 1/2000 in PBSTC for 1 h at 37° C. Wells were washed thrice and assays were developed with freshly prepared ABTS® solution (1 mg/ml) for 30 minutes at room temperature (RT) in the dark. Absorbance was measured at 405 nm in an ELISA plate reader.

Cloning and Sequence Analysis of Anti-P-selectin HuMab Variable Domains (κ-light and γ1-heavy Chains)

The nucleotide sequences coding for the light chain variable region $V_L$ and the heavy chain variable region $V_H$ of the P-selectin HuMabs were isolated by a standard cDNA synthesis/PCR procedure.

Total RNA was prepared from $1 \times 10^6$-$1 \times 10^7$ hybridoma cells using the RNeasy® Mini Kit (Qiagen). Hybridoma derived RNA was used as a template for the $1^{st}$ strand cDNA synthesis which was performed according to a conventional method making use of an oligo dT primer. $2^{nd}$-strand cDNA synthesis and further PCR amplification of $V_L$ and $V_H$ encoding cDNA fragments were performed with reverse light and heavy chain primers complementary to nucleotide sequences of the κ-light and γ1-heavy chain constant region and 5'-specific light and heavy chain primers, respectively. The PCR products were cloned using the TOPO® TA cloning kit from Invitrogen™ life technologies and pCR4-TOPO® as a cloning vector. Cloned PCR products were identified by restriction mapping of the appropriate plasmids using EcoRI for digestion and expected/calculated DNA fragment sizes of about 740 and 790 bp for $V_L$ and $V_H$, respectively.

The DNA sequence of cloned PCR fragments was determined by double strand sequencing.

The GCG® (Genetics Computer Group, Madison, Wis.) software package version 10.2 was used for general data processing. DNA and protein sequences were aligned using the GCG® modul CLUSTALW. Sequence alignments were tabulated, edited and color-coded using the program GENE-DOC® (version 2.1).

Construction of Expression Plasmids for an Anti-P-selectin IgG1 HuMab

The anti-P-selectin HuMab light and heavy chain encoding genes were separately assembled in mammalian cell expression vectors.

Thereby the gene segments encoding the anti-P-selectin HuMab light chain variable region ($V_L$) and the human κ-light chain constant region ($C_L$) were joined as were gene segments for the anti-P-selectin HuMab heavy chain variable region ($V_H$) and the human γ1-heavy chain constant region ($C_{H1}$-Hinge-$C_{H2}$-$C_{H3}$).

General information regarding the nucleotide sequences of human light and heavy chains from which the codon usage can be deduced is given in: Kabat, E. A., Wu, T. T., Perry, H. M., Gottesman, K. S., and Foeller, C. (1991) *Sequences of Proteins of Immunological Interest*, Fifth Ed., NIH Publication No 91-3242.

The transcription unit of the anti-P-selectin HuMab κ-light chain is composed of the following elements:
 The immediate early enhancer and promoter from the human cytomegalovirus (HCMV),
 A synthetic 5'-UT including a Kozak sequence,
 A murine immunoglobulin heavy chain signal sequence including the signal sequence intron, The cloned anti-P-selectin HuMab variable light chain cDNA arranged with a unique BsmI restriction site at the 5' end and a splice donor site and a unique NotI restriction site at the 3' end, The genomic human κ-gene constant region, including the intron 2 mouse Ig-κ enhancer [Picard, D., and Schaffner, W. (1984) *Nature* 307, 80-82] and The human immunoglobulin κ-polyadenylation ("poly A") signal sequence.

The transcription unit of the anti-P-selectin HuMab γ1-heavy chain is composed of the following elements:

The immediate early enhancer and promoter from the human cytomegalovirus (HCMV), A synthetic 5'-UT including a Kozak sequence, A modified murine immunoglobulin heavy chain signal sequence including the signal sequence intron, The cloned anti-P-selectin HuMab variable heavy chain cDNA arranged with a unique BsmI restriction site at the 5' and a splice donor site and a unique NotI restriction site at the 3' end, The genomic human γ1-heavy gene constant region, including the mouse Ig μ-enhancer [Neuberger, M. S. (1983) *Embo J* 2, 1373-1378], The human γ1-immunoglobulin polyadenylation ("poly A") signal sequence.

Functional elements of the anti-P-selectin HuMab κ-light chain and γ1-heavy chain expression plasmids: Beside the anti-P-selectin HuMab κ-light chain or γ1-heavy chain expression cassette these plasmids contain A hygromycin resistance gene An origin of replication, oriP, of Epstein-Barr virus (EBV)

An origin of replication from the vector pUC18 which allows replication of this plasmid in *E. coli*, and A β-lactamase gene which confers ampicillin resistance in *E. coli*.

Construction of Expression Plasmids for an Anti-P-selectin IgG4 HuMab

An anti-P-selectin γ4-heavy chain prototype expression plasmid was derived from the anti-P-selectin γ1-heavy chain expression plasmid by replacing the human genomic γ1-constant region and γ1-immunoglobulin polyadenylation ("poly A") signal sequence by the human genomic γ4-constant region and γ4-immunoglobulin polyadenylation-signal sequence.

For the expression of anti-P-selectin HuMab κ-light chains the same expression plasmids were used as described for IgG1 (see above).

Construction of Expression Plasmids for Mutant (Variant) Anti-P-selectin IgG1 and IgG4

Expression plasmids encoding mutant anti-P-selectin γ1- and γ4-heavy chains were created by site-directed mutagenesis of the wild type expression plasmids using the QuickChange™ Site-Directed mutagenesis Kit (Stratagene).

The following mutants were generated for LC1004-002. Amino acids are numbered according to EU numbering [Edelman, G. M., Cunningham, B. A., Gall, W. L., Gottlieb, P. D., Rutishauser, U., and Waxdal, M. J. (1969) *Proc Natl Acad Sci USA* 63, 78-85; Kabat, E. A., Wu, T. T., Perry, H. M., Gottesman, K. S., and Foeller, C. (1991) *Sequences of Proteins of Immunological Interest*, Fifth Ed., NIH Publication No 91-3242].

TABLE 1

| Isotype | Abbreviation | Mutations | Description |
|---|---|---|---|
| IgG1 | IgG1v1 | PVA-236; GLPSS331 as specified by E233P; L234V; L235A; delta G236; A327G; A330S; P331S SEQ ID NO: 25 | The amino acid sequence $Glu_{233}Leu_{234}Leu_{235}Gly_{236}$ (SEQ ID NO: 53) of the human γ1-heavy chain is replaced by the amino acid sequence $Pro_{233}Val_{234}Ala_{235}$ of the human γ2-heavy chain. The amino acid sequence $Ala_{327}Leu_{328}Pro_{329}Ala_{330}Pro_{331}$ (SEQ ID NO: 54) of the human γ1-heavy chain is replaced by the amino acid sequence $Gly_{327}Leu_{328}Pro_{329}Ser_{330}Ser_{331}$ (SEQ ID NO: 55) of the human γ4-heavy chain |
| IgG1 | IgG1v2 | L234A; L235A SEQ ID NO: 26 | The amino acid sequence $Leu_{234}Leu_{235}$ of the human γ1-heavy chain is replaced by the amino acid sequence $Ala_{234}Ala_{235}$ |
| IgG4 | IgG4v1 | S228P; L235E SEQ ID NO: 28 | $Ser_{228}$ of the human γ4-heavy chain is replaced by $Pro_{228}$ and $Leu_{235}$ of the human γ4-heavy chain is replaced by $Glu_{235}$ |

Production of Recombinant Anti P-selectin HuMabs

Recombinant HuMabs were generated by transient transfection of adherent HEK293-EBNA cells (ATTC # CRL-10852) cultivated in DMEM (Gibco) supplemented with 10% ultra-low IgG FCS (Gibco), 2 mM Glutamine (Gibco), 1% v/v nonessential aminoacids (Gibco) and 250 μg/ml G418 (Roche). For transfection Fugene™ 6 (Roche) Transfection Reagent was used in a ratio of reagent (μl) to DNA (μg) ranging from 3:1 to 6:1. Immunoglobulin light and heavy chains were expressed from two different plasmids using a molar ratio of light chain to heavy chain encoding plasmid from 1:2 to 2:1. HuMab containing cell culture supernatants were harvested at day 4 to 11 after transfection. Supernatants were stored at −20° C. until purification.

General information regarding the recombinant expression of human antibody in e.g. HEK293 is given in: Meissner, P., Pick, H., Kulangara, A., Chatellard, P., Friedrich, K., and Wurm, F. M. (2001) *Biotechnol Bioeng* 75, 197-203.

Determination of the Affinity of Anti-P-selectin HuMabs

Equipment:
Instrument: BIACORE® 2000
Chip: CM5
Coupling: amine coupling
Buffer: HBS (HEPES, NaCl), pH 7.4, 25° C.

For affinity measurements rabbit anti human Fcγ antibodies (Dianova) have been coupled by amine coupling to the chip surface for presentation of the antibody against P-selectin. Approximately 400 RU of anti P-selectin antibodies were bound. Recombinant P-selectin (R&D Systems) was added in various concentrations between 0-50 nM. Association was measured by P-selectin-injection for 120 seconds; dissociation was measured by washing the chip surface with buffer for 180 seconds. The affinity data for different P-selectin antibodies are shown in Table 2. Using Biaevaluation Software the kinetic data were fitted to a 1:1 Langrnuir binding model of P-selectin to the presented monoclonal antibody.

TABLE 2

Affinity data measured by SPR (BIACORE ® 2000)

| Antibody HuMab | ka (1/Ms) | kd (1/s) | KA (1/M) | KD (M) |
|---|---|---|---|---|
| 001 | $6.08 \times 10^5$ | $4.19 \times 10^{-4}$ | $1.45 \times 10^9$ | $6.89 \times 10^{-10}$ |
| 002 | $8.10 \times 10^5$ | $2.13 \times 10^{-3}$ | $3.81 \times 10^9$ | $2.63 \times 10^{-9}$ |
| 003 | $6.60 \times 10^5$ | $2.91 \times 10^{-4}$ | $2.27 \times 10^9$ | $4.41 \times 10^{-10}$ |
| 005 | $8.42 \times 10^5$ | $2.89 \times 10^{-4}$ | $2.91 \times 10^9$ | $3.43 \times 10^{-10}$ |
| 011 | $1.77 \times 10^6$ | $2.38 \times 10^{-3}$ | $7.44 \times 10^8$ | $1.34 \times 10^{-9}$ |
| 012 | $1.08 \times 10^6$ | $1.25 \times 10^{-4}$ | $8.65 \times 10^9$ | $1.16 \times 10^{-10}$ |
| 013 | $1.46 \times 10^6$ | $2.02 \times 10^{-4}$ | $7.22 \times 10^9$ | $1.39 \times 10^{-10}$ |
| 017 | $7.79 \times 10^5$ | $1.39 \times 10^{-5}$ | $5.59 \times 10^9$ | $1.79 \times 10^{-11}$ |

Inhibitory Activity of the P-selectin Antibodies in a Cell-based Adhesion and Rosetting Assay Materials and Methods:

Cell adhesion assay: In the adhesion assay the effect of the HuMabs on the adhesion of leukocyte-like HL60 cells (ATCC CCL 240) to P-selectin coated onto microtiter plates was evaluated. The HL60 cells were labelled with BCECF-AM (2',7'-bis-(2-carboxyethyl)-5-(and-6)-carboxyfluorescein acetoxymethyl ester; Cat. no 216254, Calbiochem). Full-length purified P-selectin (purification procedure s. above) at a concentration of 1 µg/ml in buffer containing 150 mM NaCl, 1 mM $CaCl_2$, IMM $MgCl_2$, 20 mM Tris (pH 7.4) plus 0.0005% Tx100 was coated overnight at 4° C. to 96 wells plates (Nunc Immunoplate Maxisorp™ F96). Thereafter, the wells were blocked with the above-mentioned buffer containing 3.5% bovine serum albumin (BSA, Fluka) for 2 h at room temperature (RT). The wells were preincubated with 50 µl of different dilutions of the P-selectin HuMabs or reference mouse P-selectin antibodies (WAPS 12.2, respective hybridoma cell line provided by ATCC) in the above-mentioned buffer containing 1% BSA for 20 minutes at RT. The labelled HL60 cells (50 µl, 70,000 cells/well) were added and allowed to bind for 45 min at RT. In some experiments the HL60 cells were preincubated with 20 µg/ml of human IgG1 for 30 minutes prior to their addition to the wells in order to block Fc receptors. After removal of the unbound HL60 cells by gentle washing (4 times with the above-mentioned buffer), the adherent cells were lysed with 120 µl NP-40 (Fluka; 1% in $H_2O$). 100 µl of the supernates were transferred to plates to measure the respective fluorescence at an excitation wavelength of 485 nm and an emission of 538 nm using a luminescence spectrometer LS 50B (Perkin Elmer).

Rosetting assay: To evaluate the effect of the antibodies on the interaction of activated platelets with HL60 cells a rosetting assay (Jungi et al., Blood 67:629 (1986)) in combination with double color cytofluorimetric analysis (Evangelista et al., Blood 88:4183 (1996) was applied. Washed human platelets were prepared as described (Fox et al, Methods Enzymol 215:45 (1992)). They were activated with thrombin (final conc 1 U/ml) for 5 min and labelled with a FITC-conjugated anti-human GPIIb antibody p1-36 (Kouns et al., J Biol Chem 267:18844 (1992)). Then $1.4-2 \times 10^6$ platelets within 70 µl of tyrode solution were incubated with different dilutions of HuMabs (100 µl) in the dark for 30 min at RT. 50 µl of HL60 cell suspension (in tyrode solution) adjusted to $20 \times 10^6$/ml was added. The HL60 cells were labeled by incubation with 20 µl of a PE (phycoerythrin)-conjugated anti-human CD45 Ab (Code No. 555483, Pharmingen). After having incubated the labeled HL60 cells with the platelets and the HuMabs for 30 min at room temperature in FACS® tubes (Becton Dickinson), the formation of mixed aggregates or rosettes was analyzed by measuring both platelet and HL60 cell marker fluorescence using a FACScan™ (Becton Dickinson). Forward and side scatter, as well as green (FITC) and red (PE) signals were acquired by logarithmic amplification with excitation wavelength of 488 nm and emission wavelength of 530 nm (FITC) and 570 nm (PE), respectively. Electronic compensation was used to remove spectral overlap. HL60 cells were identified on the basis of forward and side scatter. Gating on events identified as HL60 cells was performed to exclude single platelets. Five thousand HL60 cell-gated events were measured for each sample. A sample in which non-activated or thrombin-activated platelets were mixed with HL60 cells in the presence of EDTA (10 mmol/l) was used to set a threshold on the green fluorescence scale. The percentage of HL60 cells above the threshold represents the percentage of HL60 cell binding platelets. The shift of the platelet marker fluorescence towards lower fluorescence values reflects the reduction of the number of mixed aggregates with a higher number of adhering platelets in favor of an increase of the number of mixed aggregates with a low number of adhering platelets.

Results:

In the HL60 cell adhesion assay the P-selectin antibodies inhibited the adhesion of the HL60 cells to purified P-selectin with IC50 values in the range of 0.08-0.5 µg/ml, Although the mutations were introduced in the Fc portion of the antibody, both the IgG4 and IgG1 variants of HuMabs were more potent than the parent antibody with IC50 values of 0.08-0.11 µg/ml as illustrated in FIG. 1. When preincubating the HL60 cells with human IgG1, the potency of the parent non-mutated antibodies is also increased with an about 3 to 4-fold reduction of the IC50 value, as demonstrated for HuMab 002 in FIG. 1. This finding suggests that the increased efficacy of the mutants in the adhesion assay is primarily due to the elimination of the adhesion of the HL60 cells to P-selectin via the Fc portion of the antibody to the Fcγ receptors.

Figure 2:
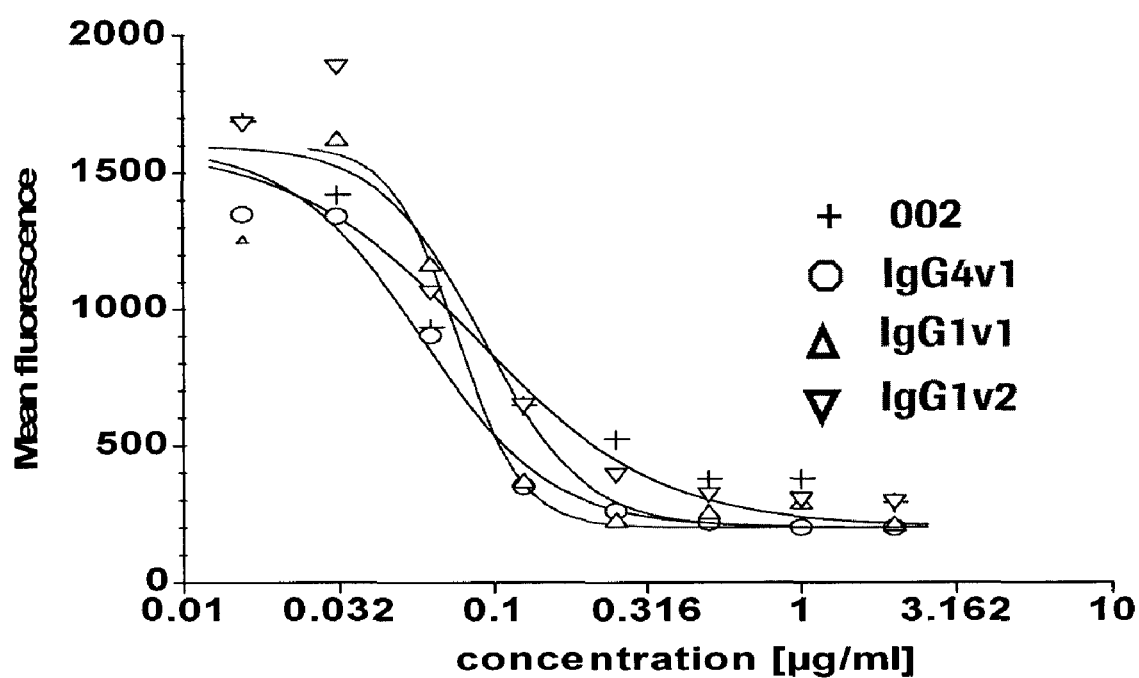
FIG. 2 shows the inhibitory activity of the antibodies of the invention in the rosetting assay measuring the adhesion of thrombin-activated platelets to HL60 cells.

In the rosetting assay evaluating the adhesion of human activated platelets expressing P-selectin to HL60 cells the IC50 values of the HuMabs were even below those of the adhesion assay due to the lower number of P-selectin receptors in this assay (IC50: 0.05-0.3 µg/ml, preferably between 0.05 and 0.2 µg/ml). The efficacy of the Fc variants of the respective HuMabs tends to be increased as compared to the non-mutated parent antibody (FIG. 2). Preincubation of the HL60 cells with IgG1 and IgG4 prior to the incubation with the activated platelets did not significantly affect the inhibitory activity of both the mutants and the parent antibody, indicating a less pronounced role of the Fcγ receptor-mediated binding in the rosetting assay as compared to the adhesion assay.

Cross-reactivity of the P-selectin Antibodies with P-selectin from Animal Species Materials and Methods: The cross-reactivity of the P-selectin HuMabs was evaluated by measuring (i) the binding of the HuMabs to activated platelets from rat and cynomologus monkey using FACS® analysis and (ii) their inhibitory activity in the rosetting assay evaluating the adhesion of rat and cynomologus platelets to HL60 cells.

To measure the binding of the HuMabs to activated rat and cynomologus platelets, washed rat and cynomologus platelets were prepared similar to preparing washed human platelets (s. above). They were activated with thrombin (final conc 1 U/ml) for 5 min. Activated platelets were incubated with different dilutions of the HuMabs (20 µl) for 30 min at RT. After binding of the HuMabs the platelets were fixed with PFA 2% at RT for 15 min. Samples were washed with Tyrode buffer and resuspended in 300 ml Tyrode. The binding of the HuMabs was detected with a FITC-conjugated F(ab')$_2$ fragment of rabbit anti-human IgG (Code No. F0056, Dako). As a control antibody inhibiting rat P-selectin a rabbit anti-human polyclonal anti-P-selectin antibody (Code No. 09361A, Pharmingen) was used.

To measure the inhibitory effect of the P-selectin HuMabs in the rosetting assay, washed rat and cynomologus platelets were prepared as described above for human platelets. The rosetting assay was performed essentially as described for human platelets. For the labelling of the cynomologus platelets the FITC-conjugated anti-human GPIIb antibody p1-36 was used, whereas the rat platelets were labeled with the FITC-conjugated mouse anti-rat CD61 antibody (Code No. 554952, Pharmingen).

Figure 3A:
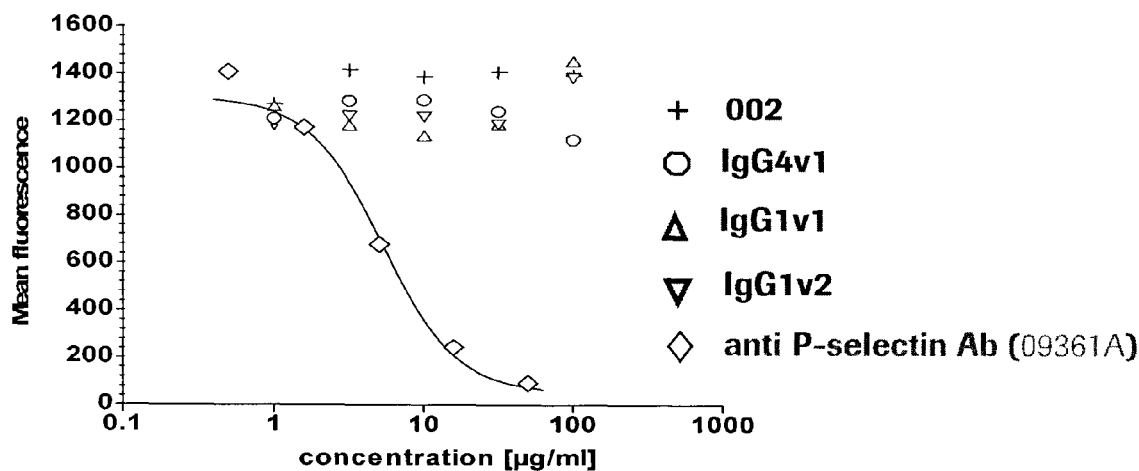
FIGS. 3a and 3b depicts the cross-reactivity of the antibodies of the invention with rat and cynomologus P-selectin.
Figure 3B:
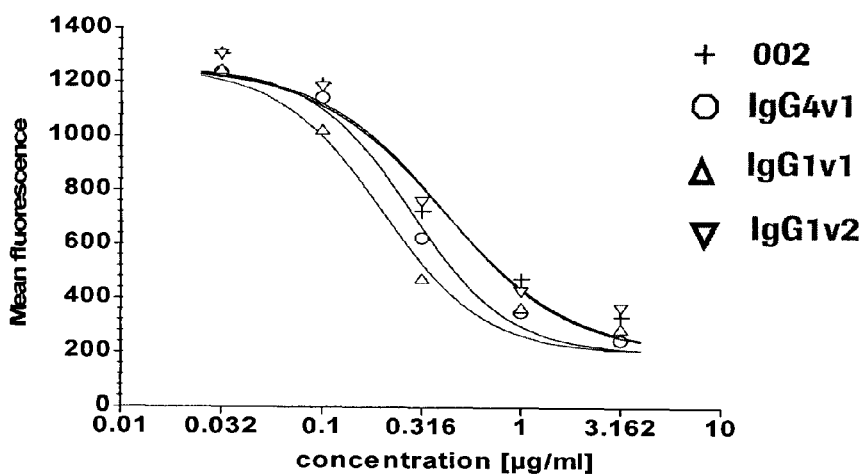

Results: None of the P-selectin specific antibodies of the invention which inhibit human P-selectin-mediated functions was shown to bind to rat P-selectin or to inhibit the formation of mixed aggregates consisting of rat platelets and HL60 cells, as shown for some examples in FIG. 3a. However, the P-selectin HuMabs bind to and inhibit cynomologus P-selectin (FIG. 3b).

Selectivity of the P-selectin Antibodies vs E- and L-selectin

Materials and Methods: The selectivity of the P-selectin HuMabs vs E- and L-selectin was determined in a cell-free ELISA measuring the binding of the antibodies to recombinant E- and L-selectin (ADP1 and ADP2, R&D Systems) and a cell-based ELISA measuring the binding of the antibodies to E-selectin-CHO transfectants and L-selectin-300.19 transfectants (transfectants were generated as described in Goetz et al., J Cell Biol 137:509 (1997); Ley et al., Blood 82:1632 (1993)).

In the cell-free ELISA recombinant P-, E-, or L-selectin at a concentration of 1 µg/ml in buffer containing 150 mM NaCl, 1 mM CaCl$_2$, 1 mM MgCl$_2$, 20 mM Tris (pH 7.4) plus 0.0005% Tx100 was coated overnight at 4° C. to 96 well plates (Nunc Immunoplate Maxisorp F96). Thereafter, the wells were blocked with the above-mentioned buffer containing 3.5% bovine serum albumin (BSA, Fluka) for 2 h at RT. The wells were preincubated with 50 µl of different dilutions of the P-selectin HuMabs or reference mouse P-, E-selectin antibody (BBA26; R&D Systems) and goat L-selectin antibody (AF728; R&D Systems) in the above-mentioned buffer containing 1% BSA overnight at RT. The binding of the HuMabs was detected by using a biotinylated anti-human IgG (Amersham, RPN1003, Final concentration 1:1000) or for the control antibodies the corresponding biotinylated anti-mouse or anti-goat IgG. After 1 h incubation, the wells were washed (3 times) with the above-mentioned buffer, and 0.1 ml of streptavidin-biotinylated peroxidase complex (Amersham, RPN1051), diluted 1:750 in the mentioned buffer containing 0.1% BSA was added for 30 min. The wells were then washed and 0.2 ml of peroxidase substrate solution containing ABTS (2.2'-azino-di-(3-ethylbenzthiazoline sulfonate, Boehringer, Mannheim) was added (ABTS stock solution: 1 ml 40 mM ABTS, 5 µl 30% $H_2O_2$ and 20 ml 0.1M Na-Acetat, 0.05 NaH2PO4). The reaction was stopped after around 10 min using 50 µl of 0.1 M citrate and 0.01% NaN3. The color reaction was read at 405 nm.

In the cell-based ELISA P- and E-selectin-CHO-transfectants, after detaching the cells with cell-dissociation solution (Sigma C5914), were seeded into each well of 96 well plates (TC Microwell F96 Nunc 167008) adjusted to 100,000 cells/well and cultivated in respective media overnight at 37° C. (medium for P-CHO-transfectants: DMEM+10% FCS+2 mM Glutamine+Penicillin 100 U/ml/Streptomycin 100 µg/ml; medium for E-selctin transfectants: HAM F-12+10% FCS+2 mM Glutamine+Penicillin 100 U/ml/Streptomycin 100 µg/ml+0.1% Fungizone+100 µg/ml Neomycin). After removal of the media and blocking the wells with A-T buffer (150 mM NaCl, 1 mM CaCl$_2$, 1 mM MgCl$_2$, 20 mM Tris (pH 7.4)) containing 3% TopBlock™ (Code No. TB232010; Juro) for 1 h, 50 µl of different dilutions of the P-selectin HuMabs or reference mouse P- and E-selectin antibody (s. above) in the above-mentioned buffer containing 1% TopBlock™ and 0.1% azide were added and incubated for 60 min at RT. After washing the wells (4 times), the bound antibodies were detected using the same steps as mentioned above for the cell-free ELISA.

Since the L-selectin 300.19 cells are suspension cells, the cell-based ELISA format had to be modified by plating the L-selectin-300.19 transfectants into wells of 96 well polystyrene filter plates (Corning 3510). Using the filter plates blocking and incubation solutions were removed by filtering them through the bottom of the plates, but otherwise the protocol was similar to that using P- and E-selectin-CHO cells. As controls non-transfected CHO and 300.19 were used.

Figure 4A:
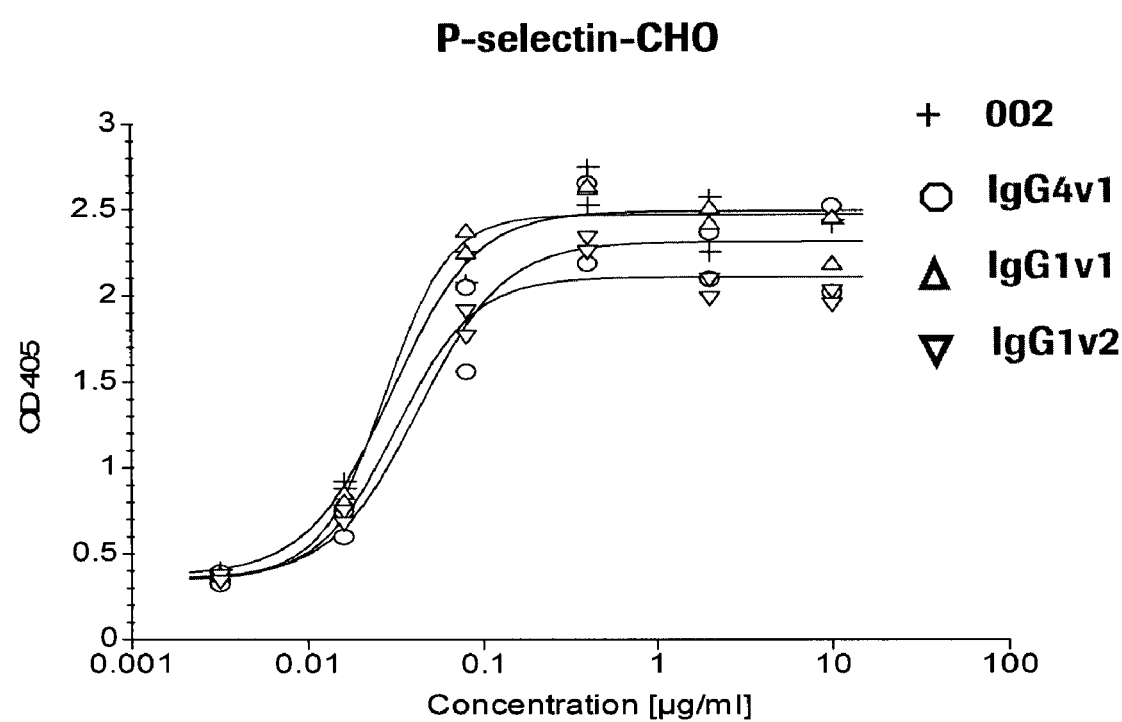
FIG. 4a-c demonstrates the selectivity of the antibodies for P-selectin vs. E- and L-selectin by representative binding curves on P-, E- and L-selectin transfectants. The antibodies according to the invention bind to P-selectin CHO cells with $EC_{50}$ values in the range of 0.01 and 0.07 µg/ml. $EC_{50}$ values on E-selectin CHO cells and L-selectin 300.19 cells are preferably above 100 µg/ml.
Figure 4B:
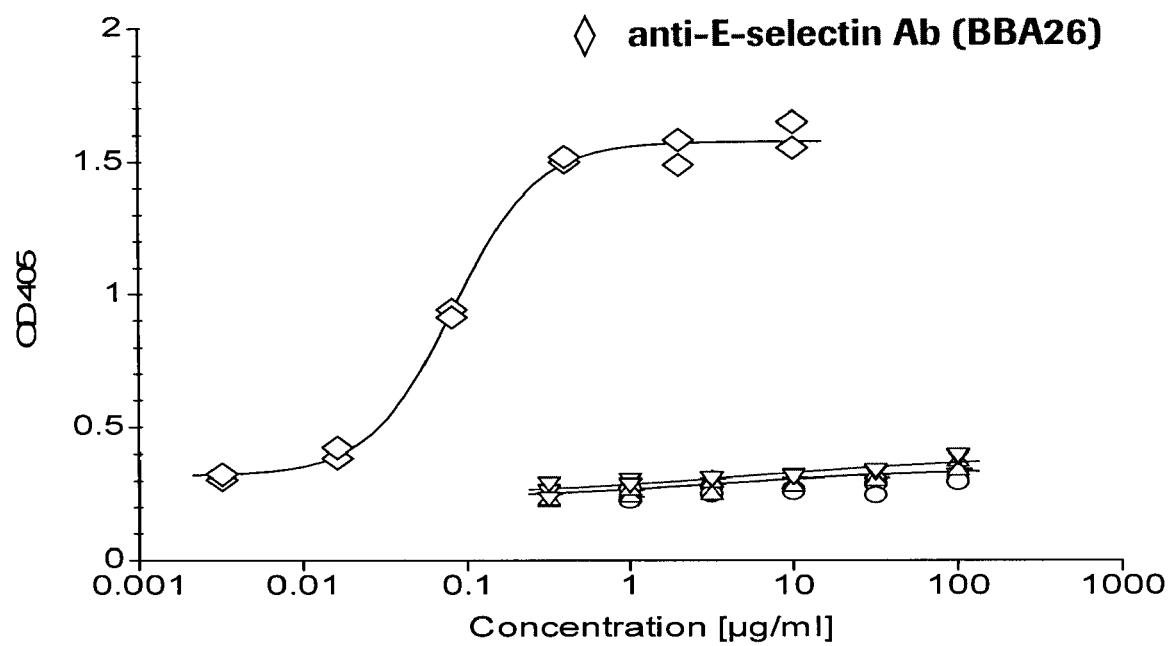
Figure 4C:
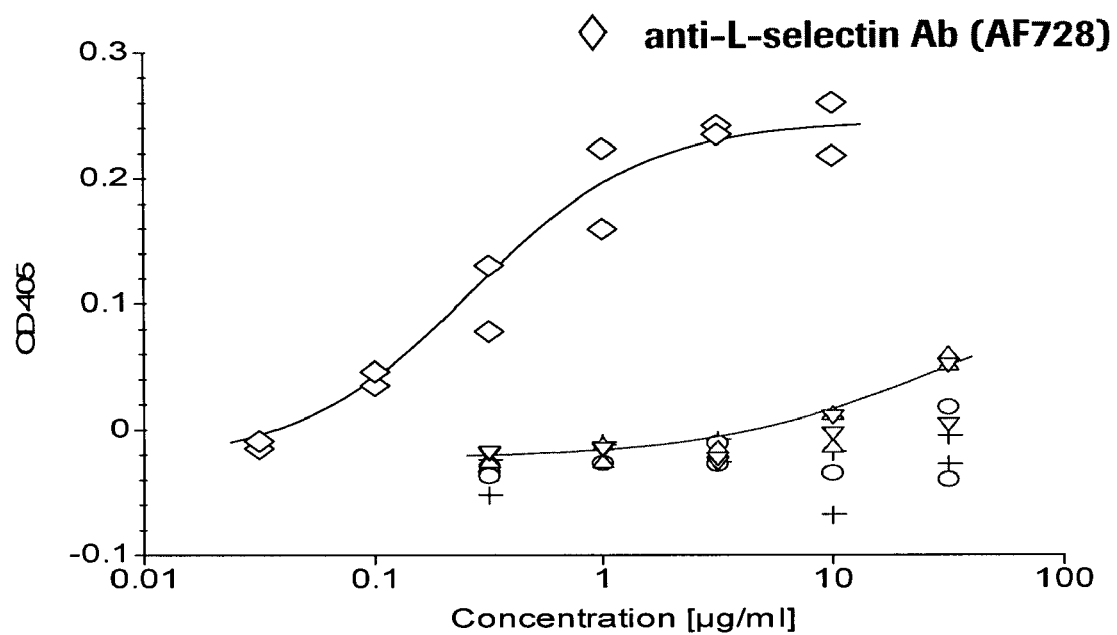

Results:
The antibodies of the invention were highly selective vs E- and L-selectin. They bound to P-selectin-CHO cells with EC50 values in the range of 0.01 to 0.08 µg/ml, preferably in the range of 0.01 to 0.04 µg/ml, whereas the EC50 values on E-selectin-CHO cells and L-selectin-300.19 were clearly above 50 µg/ml, preferably above 100 µg/ml. HuMab 002 had highest selectivity with a selectivity factor vs E- and L-selectin of more than 4,000 fold in the cell-based ELISA. Furthermore HuMab 002 does not bind to E- and L-selectin transfectants above baseline levels up to a concentration of 100 µg/ml. The selectivity of the Fc variants IgG4v1 and IgG1 v1 of HuMab 002 is similar to that of the parent HuMab 002 (FIG. 4a-c).

Ex vivo Inhibitory Activity of P-selectin Antibodies in a Fully Human Blood Flow System Effect of P-selectin HuMabs on Leukocyte Adhesion to a Platelet Monolayer Materials and Methods:
To address the effect of the P-selectin antibodies on the recruitment of leukocytes to sites of vessel wall injury and platelet thrombi, a human blood flow system which allows the measurement of the interaction of human leukocytes with human platelets at different shear rates was used essentially as described (Kirchhofer et al., Blood 89:1270 (1997)). In a parallel plate perfusion device human whole blood drawn from the antecubital vein of a healthy donor was perfused over a collagen surface simulating an injured denuded vessel wall. Collagen-coated coverslips were prepared as described (Kirchhofer et al., Blood 89:1270 (1997)). They were positioned in three parallel plate perfusion chambers. To allow the measurement of different shear rates (65/s and 280/s) different dimensions of perfusion chambers were used and the blood was perfused over the collagen-coated coverslips at a constant blood flow of 1 ml/min which was controlled by individual roller pumps positioned distal to the perfusion device. Immediately after drawing the blood from the vein and separating the blood into three tubings, a GPIIb/IIIa inhibitor (0.5 µmol/lamifiban) is added to prevent platelet aggregation and to generate platelet monolayers. At the same time, the P-selectin antibodies (the HuMabs, mutants, respective reference antibodies or human IgG1 and IgG4 as controls) were administered at different concentrations and the blood-inhibitor mixture then entered the perfusion chamber containing the collagen-coated coverslips. After a 5.5 minute perfusion period, PBS is perfused through the perfusion chamber without interrupting the flow for 3 min. After a brief interruption of flow the chambers were fixed with 3% paraformaldehyde in PBS at 1 ml/min for 2 min. Then the coverslips were removed from the chambers, fixed again for 1 h in 3% paraformaldehyde in PBS at 4° C. and stored in PBS-0.03% sodium azide. To evaluate the number of leukocytes adhering to the platelet monolayer, after air-drying the coverslips were stained with Diff-Quick™ solution (Dade Behring AG) and embedded in Merckoglas™ (Merck, Germany). An image analysis system (MCID, Imaging Research Inc.) was used to determine the number of leukocytes adhering to a standard area oriented perpendicular to the blood flow 1 mm apart from the beginning of the coverslip. At a shear rate of 65/s and 280/s the area on which the number of leukocytes was counted comprised 3.1 mm$^2$ and 2.1 mm$^2$, respectively.

Figure 5:
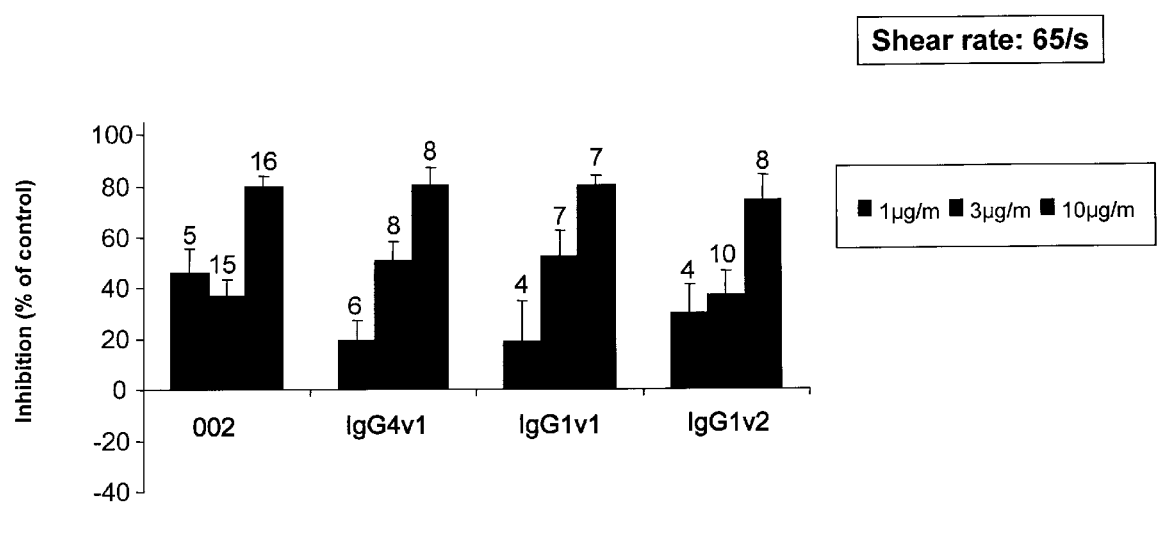
FIG. 5 depicts the inhibitory activity of the antibodies of the invention in a fully human flow system. They inhibit the adhesion of human leukocytes to a platelet monolayer in a concentration-dependent manner at a shear rate of 65/s.

Results:

The P-selectin HuMabs inhibited the adhesion of leukocytes to the platelet monolayer in a concentration-dependent manner. At a shear rate of 65/s and a concentration of 10 µg/ml the HuMabs inhibited the adhesion of leukocytes by 60-99%, preferably 70-99%. The inhibitory effect of the HuMabs was more pronounced at the higher shear rate of 280/s (closer to the arterial situation) as compared to the venous shear rate of 65/s. Overall, at a shear rate of 280/s the number of adhering leukocytes was lower than at 65/s. When comparing the Fc variants with the respective parent antibodies, they had similar inhibitory activity in the ex vivo perfusion chamber, as demonstrated for HuMab 002 and its variants IgG4v1 and IgG1v1 (FIG. 5). The increased inhibitory activity of the mutants vs the parent antibody found in the in vitro assays was not observed in the ex vivo perfusion chamber which may be due to the saturation of the Fcγ receptors of the leukocytes in whole human blood.

Effect of P-selectin HuMabs on Leukocyte Adhesion to Endothelial Cells

Materials and Methods:

To address the anti-inflammatory potential of the P-selectin HuMabs under shear conditions, the above-mentioned human blood flow system was used in a set up in which endothelial cells were coated onto the coverslips. Human umbilical vein endothelial cells (HUVEC) from umbilical cords were isolated by digestion with collagenase Type II (Roche Switzerland) according to the method of Jaffe et al, Culture of human endothelial cells derived from umbilical veins. J. Clin. Invest. 52, 2745-2756 (1973). They were cultivated in 1% gelatine-coated tissue culture flasks in medium 199 (M199, Sigma, Germany) supplemented with 20% fetal calf serum (Gibco, Auckland), 100 IU/ml penicillin (Gibco, Auckland), 0.1 mg/ml streptomycin (Gibco, Auckland), 2 mmol/l L-glutamine (Gibco, Auckland), 10 U/ml heparin (Sigma) and 50 µg/ml EC growth supplement (Sigma, Germany). HUVECs were grown to confluency (approx. 4 days), passaged with trypsin/ethylendiaminetetraacetic acid (Gibco, Auckland) and seeded onto Thermanox® plastic coverslips (approx 200,000 ECs/coverslip) previously coated with 1% gelatine (Fluka, Germany). The HUVECs were allowed to settle and became confluent over 1-2 days. They were stimulated with 20 ng/ml IL-4 (R&D Systems) 24 h before starting the perfusion and with $10^{-4}$ M histamine (Fluka, Germany) 5-10 min prior to the perfusion. Each experiment was performed with HUVECs at passage 1. The coverslips with confluent monolayers of stimulated HUVECs were positioned into the parallel plate perfusion chambers as described above. Similar to the perfusion experiments described above, whole blood was drawn from healthy donors. However in these experiments, the blood was anticoagulated with a thrombin inhibitor Ro-46-6240 (10 µM) and preincubated with different concentrations of the P-selectin antibodies (HuMabs, mutants, respective reference antibodies) or human IgG1 and IgG4 as controls for 5 min just prior to the perfusion over the activated endothelial cells. The blood flow was adjusted to 1 ml/min, the shear rate 65/s and the perfusion time 5.5 min. After a washing period of 3 min with PBS, the HUVECs with the adhering leukocytes were fixed with 3% paraformaldehyde for 2 min under the same flow conditions as described. Then the coverslips were removed from the chambers, immersed in fresh fixative for 1 h, and stored in PBS-0.02% sodium azide. For morphometric analysis, the leukocytes were stained with a mouse antibody against the leukocyte common antigen CD45, which was labeled beforehand using a modified biotinylated anti-mouse immunoglobulin (Animal Research Kit, Dako, USA). The nuclei were counterstained with hematoxylin (J. T Baker, Holland).

Results:

The stimulation of the HUVECs with the combination of IL-4 and histamine resulted in the expression of P-selectin and the adhesion of different types of leukocytes with granulocytes (including PMNs and eosinophils) constituting the prevailing portion of adhering leukocytes. The HuMabs of the invention inhibited the adhesion of the total leukocyte population by 60-90% at 3 µg/ml. Overall the inhibitory activity of the Fc variants was not significantly different from that of the non-mutated HuMabs.

The P-selectin HuMabs demonstrate a differential effect on the different leukocyte subtypes. The effect on granulocytes is more pronounced as compared to mononuclear leukocytes. The antibodies according to the invention inhibited the adhesion of granulocytes (including PMNs and eosinophils) by 90-99%, monocytes by 50-88%, and lymphocytes by 5-40%.

Figure 6A:
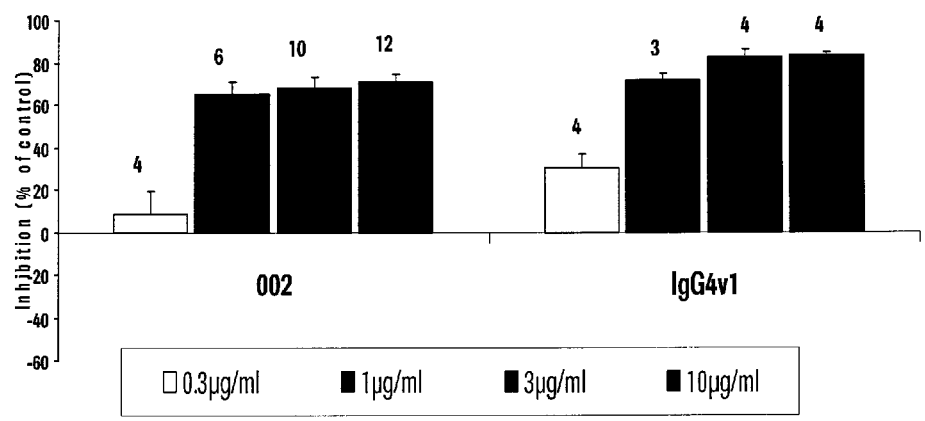
FIG. 6a demonstrates the total inhibition of leukocyte adhesion in % of the control, FIG. 6b representatively shows the inhibitory effect of one of the antibodies on the absolute number of the different leukocyte subsets.
Figure 6B:
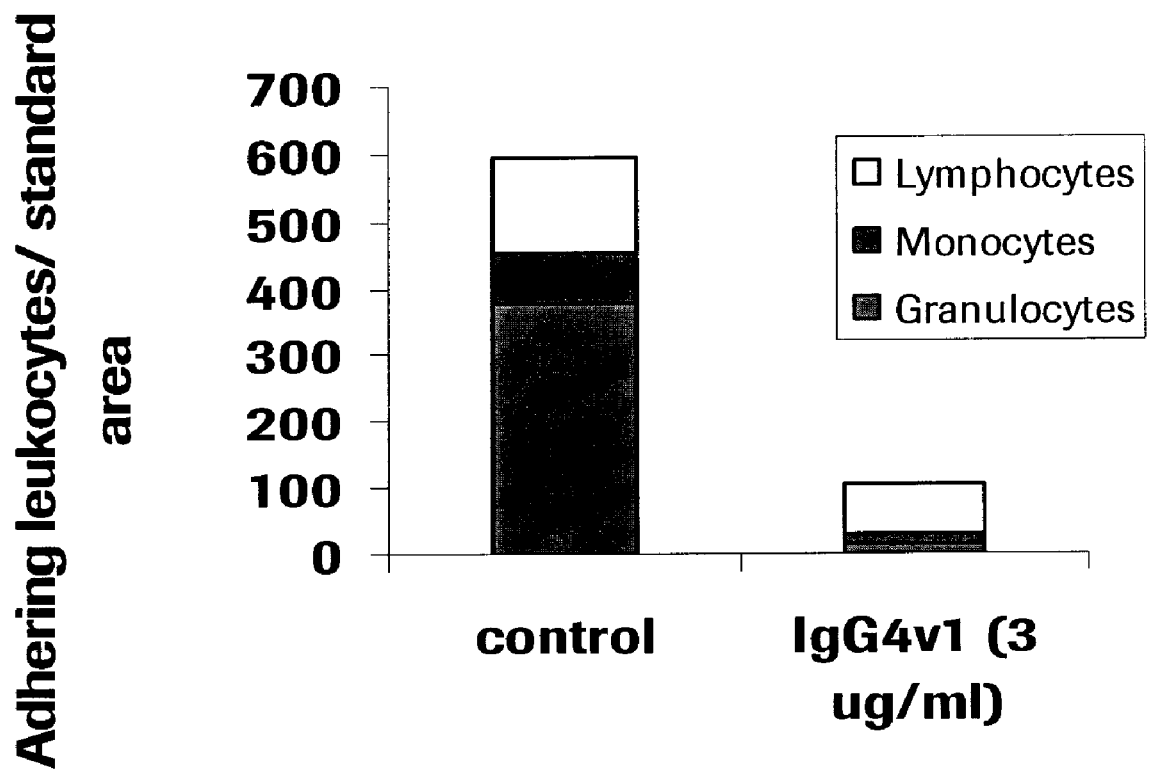
FIG. 6 depicts the inhibitory effect of the antibodies of the invention on the adhesion of leukocytes to human endothelial cells expressing P-selectin.

The respective decrease in the absolute numbers of the different leukocyte subtypes is representatively given for IgG4v1 in FIG. 6.

Potential of P-selectin HuMabs to Activate Complement System

C1q and C3c Binding ELISA:

To determine the ability of the antibodies of the invention to induce C1q binding and C3 activation, an ELISA approach was used. C1q is part of the adaptive immune system and, upon binding to immune complexes, triggers the sequential activation of several zymogens. The enzymes in turn, cause the cleavage of C3 molecules, which can result in the onset of inflammatory reactions, opsonization of foreign or aberrant particles and lysis of cell membranes.

In principle, the ELISA plate is coated with concentration ranges of the antibody, to which human C1q or human pooled serum, as a source of C3, is added. C1q or C3ε binding is detected by an antibody directed against human C1q or C3ε followed by a peroxidase-labeled conjugate.

HuMab 002 (the hybridoma- and the transient transfectoma-derived material, its mutant variants, and control antibodies were tested in concentrations of 0.16-20 μg/ml. As a negative control a human IgG4 (CLB, the Netherlands, 0.5 μg/ml stock), that binds C1q very weakly, was used. Human IgG1 (Sigma, 2 ug/ml stock) was incorporated as positive control. For the detection of C1q, a rabbit antibody directed against C1q (Dako) and a swine anti-rabbit IgG antibody, conjugated with horseradish peroxidase (Sigma) were used. For the detection of C3ε a mouse anti-human C3 antibody and a rabbit anti-mouse IgG antibody, conjugated with horseradish peroxidase (Sigma) were applied.

Calculations concerning EC50 values or maximum binding at 10 μg/ml (Bmax) of the HuMab tested were determined using nonlinear regression curve fitting (one site binding) using Graphpad® Prism software.

Results:

HuMab 002 according to the invention was able to bind C1q efficiently as indicated by EC50 values of 0.946 μg/ml and 1.159 μg/ml, and Bmax (OD405) values of 0.987 and 0.711 for the hybridoma- and transfectoma-derived material, respectively. As expected, the negative control human IgG4 did not bind C1q, as indicated by a Bmax value of 0.222 at OD405. However, all three Fc-variants tested (IgG4v1, IgG1v1, IgG1v2) had lost the capacity to bind C1q, as shown by OD405 Bmax values of 0.132, 0.119, and 0.132, respectively (Table 3). In line with the C1q binding capacities, C3 deposition to HuMab 002 (hybridoma- and transfectoma-derived) occurred in an antibody-concentration dependent manner, and EC50 values ranged between 2.7 μg/ml and 8.3 μg/ml. However, all three Fc-variants were unable to initiate C3 deposition, as indicated by OD405 Bmax values of 0.104, 0.156 and 0.133, respectively (Table 3).

As HuMab 002 interacts with complement components, this antibody has the intrinsic potential to induce CDC in vivo. Therefore, the Fc part of this antibody is modified according to the invention.

TABLE 3

| | C1q ELISA | | C3 ELISA | |
| | Bmax | | | |
| | (OD405 at 10 μg/ml) | Background (OD405) | Bmax (OD405 at 10 μg/ml) | Background (OD405) |
|---|---|---|---|---|
| HuMab 002 (hybridoma) | 0.987 | 0.079 | 4.47 | 0.098 |
| IgG4v1 | 0.132 | | 0.104 | |
| IgG1v1 | 0.0119 | | 0.156 | |
| IgG1v2 | 0.132 | | 0.133 | |
| HuMab 002 (transient) | 0.711 | | 4.071 | |
| IgG4 | 0.222 | | 0.182 | |

Potential of P-selectin HuMabs to Bind to Fcγ Receptors

IgG antibody dependent cytotoxicity effects are mediated by Fcγ receptors on effector cells. Binding of hybridoma- and transfectoma-derived HuMab 002 as well as the mutant variants and control antibodies to FcγR expressing effector cells from human blood was studied by FACS® analysis.

Materials and Methods:

FcγRI IIA1.6 transfectants or freshly isolated effector cells were incubated with antibodies, and binding of antibody was detected with FITC-labeled rabbit-anti-human IgG F(ab)$_2$ (DAKO), or FITC-labeled rabbit-anti-human IgG F(ab)$_2$ (BD/Pharmingen). HuMab 002 (transient transfectoma- and/or hybridoma-derived material, and mutant variants) was tested at a concentration of 1 μg/ml (IIA1.6 transfectants) or 10 μg/ml (effector cells). Absence of primary antibody or human IgG4 (10 μg/ml) was used as negative control. To detect FcγRI expression on IIA1.6 cells, FITC-labeled mouse anti-human CD64 (BD/Pharmingen) was used. In experiments using NK cell-enriched peripheral blood mononuclear cells, NK cells were identified by double staining using PE-labeled mouse-anti-human CD56 (BD/Pharmingen). Granulocytes and monocytes were identified based on FSC/SSC profile.

IIA1.6 cells, IIA1.6-FcγRI transfectant and freshly isolated effector cells were incubated with antibodies. Binding of antibody was detected with FITC-labeled Rb-α-huIgG F(ab)$_2$ (DAKO), or FITC-labeled Rb-α-huIgG F(ab)$_2$ (BD/Pharmingen).

HuMab 002 (transient transfectoma-, hybridoma derived- and mutant variant material) was tested at a concentration of 1 μg/ml in the IIA1.6-FcγRI transfectant binding assay. The IIA1.6 wild type cells were used as a negative control. As a control for FcγRI expression m-α-huCD64-FITC (BD/Pharmingen) was used.

HuMab 002 (transient transfectoma-, hybridoma derived- and mutant variant material) was tested at a concentration of 10 μg/ml in the effector cell binding assays. Transient transfectoma material was not tested in the granulocyte binding assay. IgG4 (10 μg/ml) was used as a negative control in all effector cell binding assays with the exception of the granulocyte binding assay.

Whole blood was enriched for NK cells using an NK isolation kit (Dynal Biotech ASA, Oslo, Norway). NK cells were identified by m-α-huCD56-FITC staining.

PBMCs (peripheral blood mononuclear cells) were obtained from whole blood using Ficoll procedure as described in the protocol enclosed with the NK isolation kit (Dynal Biotech ASA, Oslo, Norway). Monocytes were identified based on FSC/SSC profile. Granulocytes were isolated from whole blood using FACS® lysis buffer and identified based on FSC/SSC profile.

Freshly isolated effector cells were incubated with antibodies, and binding of antibody was detected with FITC-labeled rabbit-anti-human IgG F(ab)$_2$ (DAKO), or FITC-labeled rabbit-anti-human IgG F(ab)$_2$ (BD/Pharmingen). HuMab 002 (transient transfectoma- and/or hybridoma-derived material, and mutant variants) were tested at a concentration of 10 μg/ml. Absence of primary antibody or human IgG4 (10 μg/ml) was used as negative control. NK cells were isolated from MNC samples by a NK isolation kit (Miltenyi Biotec, USA). In experiments using NK cell-enriched peripheral blood mononuclear cells, NK cells were identified by double staining using PE-labeled mouse-anti-human CD56 (BD/Pharmingen). Granulocytes and monocytes were isolated according to the state of the art from PBMC (e.g. Monocyte isolation kit (Miltenyi, see above). Granulocytes and monocytes were identified based on FSC/SSC profile.

Results:

HuMab 002 according to the invention was able to bind to FcR as indicated by binding to granulocytes, monocytes and NK cells. All three Fc-variants tested (IgG4v1, IgG1v1 and IgG1v2) had completely lost the capacity to bind to NK cells (Table 4). In addition, HuMab 002 bound efficiently to granulocytes and monocytes, whereas the mutant variants showed binding levels comparable to absence of primary antibody or human IgG4, as indicated by percentages of cells binding antibody in Tables 5 and 6. This indicates that the mutant variants lost the capacity to interact with FcR on effector cells.

As HuMab 002 can efficiently interact with FcR, this antibody has the intrinsic potential to induce antibody dependent cell-mediated cytotoxicity in vivo. Inactivation of the interaction with FcR as performed for the Fc-variants according to the invention prevents ADCC in an effective manner.

TABLE 4

| Antibody | NK cell binding (% NK cells binding antibody) |
|---|---|
| No antibody | 0.03 |
| HuMab 002 (hybridoma) | 90.92 |
| HuMab 002 (transient) | 37.40 |
| Human IgG4 | 0.06 |
| IgG4v1 | 0.06 |
| IgG1v1 | 0.12 |
| IgG1v2 | 0.00 |

TABLE 5

| Antibody | Monocyte binding (% monocytes binding antibody) |
|---|---|
| No antibody | 8.5 |
| HuMab 002 (hybridoma) | 38.4 |
| HuMab 002 (transient) | 31.3 |
| Human IgG4 | 9.4 |
| IgG4v1 | 14.5 |
| IgG1v1 | 12.3 |
| IgG1v2 | 14.0 |

TABLE 6

| Antibody | Granulocyte binding (% granulocytes binding antibody) |
|---|---|
| No antibody | 1.2 |
| HuMab 002 (hybridoma) | 63.6 |
| IgG4v1 | 1.6 |
| IgG1v1 | 2.1 |
| IgG1v2 | 2.0 |

The invention claimed is:

1. A nucleic acid molecule encoding a humanized antibody that binds to P-selectin selected from the group consisting of:
   (a) a nucleic acid molecule encoding an antibody wherein the light chain variable region comprises 3 complementarity determining regions having the amino acid sequences of: SEQ ID NO: 43 for CDR1, SEQ ID NO: 45 for CDR2, and SEQ ID NO: 47 for CDR3; and the heavy chain variable region comprises 3 complementarity determining regions having the amino acid sequences of: SEQ ID NO: 29 for CDR1, SEQ ID NO: 33 for CDR2, and SEQ ID NO: 38 for CDR3;
   (b) a nucleic acid molecule encoding an antibody wherein the light chain variable region comprises 3 complementarity determining regions having the amino acid sequences of: SEQ ID NO: 43 for CDR1, SEQ ID NO: 45 for CDR2, and SEQ ID NO: 48 for CDR3; and the heavy chain variable region comprises 3 complementarity determining regions having the amino acid sequences of: SEQ ID NO: 30 for CDR1, SEQ ID NO: 34 for CDR2, and SEQ ID NO: 39 for CDR3;
   (c) a nucleic acid molecule encoding an antibody wherein the light chain variable region comprises 3 complementarity determining regions having the amino acid sequences of: SEQ ID NO: 44 for CDR1, SEQ ID NO: 46 for CDR2, and SEQ ID NO: 49 for CDR3; and the heavy chain variable region comprises 3 complementarity determining regions having the amino acid sequences of: SEQ ID NO: 31 for CDR1, SEQ ID NO: 35 for CDR2, and SEQ ID NO: 40 for CDR3;
   (d) a nucleic acid molecule encoding an antibody wherein the light chain variable region comprises 3 complementarity determining regions having the amino acid sequences of: SEQ ID NO: 44 for CDR1, SEQ ID NO: 46 for CDR2, and SEQ ID NO: 49 for CDR3; and the heavy chain variable region comprises 3 complementarity determining regions having the amino acid sequences of: SEQ ID NO: 32 for CDR1, SEQ ID NO: 36 for CDR2, and SEQ ID NO: 41 for CDR3;
   (e) a nucleic acid molecule encoding an antibody wherein the light chain variable region comprises 3 complementarity determining regions having the amino acid sequences of: SEQ ID NO: 43 for CDR1, SEQ ID NO: 45 for CDR2, and SEQ ID NO: 50 for CDR3; and the heavy chain variable region comprises 3 complementarity determining regions having the amino acid sequences of: SEQ ID NO: 32 for CDR1, SEQ ID NO: 36 for CDR2, and SEQ ID NO: 41 for CDR3;
   (f) a nucleic acid molecule encoding an antibody wherein the light chain variable region comprises 3 complementarity determining regions having the amino acid sequences of: SEQ ID NO: 43 for CDR1, SEQ ID NO: 45 for CDR2, and SEQ ID NO: 50 for CDR3; and the heavy chain variable region comprises 3 complementarity determining regions having the amino acid sequences of: SEQ ID NO: 31 for CDR1, SEQ ID NO: 35 for CDR2, and SEQ ID NO: 40 for CDR3;
   (g) a nucleic acid molecule encoding an antibody wherein the light chain variable region comprises 3 complementarity determining regions having the amino acid sequences of: SEQ ID NO: 44 for CDR1, SEQ ID NO: 46 for CDR2, and SEQ ID NO: 51 for CDR3; and the heavy chain variable region comprises 3 complementarity determining regions having the amino acid sequences of: SEQ ID NO: 29 for CDR1, SEQ ID NO: 37 for CDR2, and SEQ ID NO: 42 for CDR3;
   (h) a nucleic acid molecule encoding an antibody wherein the light chain variable region comprises 3 complementarity determining regions having the amino acid sequences of: SEQ ID NO: 44 for CDR1, SEQ ID NO: 46 for CDR2, and SEQ ID NO: 51 for CDR3; and the heavy chain variable region comprises 3 complementarity determining regions having the amino acid sequences of: SEQ ID NO: 29 for CDR1, SEQ ID NO: 37 for CDR2, and SEQ ID NO: 42 for CDR3; and
   (i) a nucleic acid molecule encoding an antibody wherein the light chain variable region comprises 3 complementarity determining regions having the amino acid sequences of: SEQ ID NO: 43 for CDR1, SEQ ID NO: 45 for CDR2, and SEQ ID NO: 52 for CDR3; and the heavy chain variable region comprises 3 complementarity determining regions having the amino acid sequences of: SEQ ID NO: 29 for CDR1, SEQ ID NO: 37 for CDR2, and SEQ ID NO: 42 for CDR3.

2. A nucleic acid molecule of claim 1 encoding an antibody comprising a heavy chain constant region having an amino acid sequence of SEQ ID NO: 25, SEQ ID NO: 26, or SEQ ID NO: 28.

3. A nucleic acid molecule of claim 1 encoding an antibody comprising a light chain variable region comprising 3 complementarity determining regions having the amino acid sequences of: SEQ ID NO: 43 for CDR1, SEQ ID NO: 45 for CDR2, and SEQ ID NO: 48 for CDR3; and a heavy chain variable region comprising 3 complementarity determining regions having the amino acid sequences of: SEQ ID NO: 30 for CDR1, SEQ ID NO: 34 for CDR2, and SEQ ID NO: 39 for CDR3.

4. A nucleic acid molecule of claim 3 encoding an antibody comprising a heavy chain constant region having the amino acid sequence of SEQ ID NO: 28.

5. A nucleic acid molecule of claim 3 encoding an antibody comprising a light chain constant region having the amino acid sequence of SEQ ID NO: 23.

6. A nucleic acid molecule of claim 3 encoding an antibody comprising a heavy chain constant region having the amino acid sequence of SEQ ID NO: 28 and a light chain constant region having the amino acid sequence of SEQ ID NO: 23.

7. A nucleic acid molecule of claim 1 selected from the group consisting of:
- (a) a nucleic acid molecule encoding an antibody wherein the light chain variable region has the amino acid sequence of SEQ ID NO: 1 and the heavy chain variable region has the amino acid sequence of SEQ ID NO: 2;
- (b) a nucleic acid molecule encoding an antibody wherein the light chain variable region has the amino acid sequence of SEQ ID NO: 3 and the heavy chain variable region has the amino acid sequence of SEQ ID NO: 4;
- (c) a nucleic acid molecule encoding an antibody wherein the light chain variable region has the amino acid sequence of SEQ ID NO: 5 and the heavy chain variable region has the amino acid sequence of SEQ ID NO: 6;
- (d) a nucleic acid molecule encoding an antibody wherein the light chain variable region has the amino acid sequence of SEQ ID NO: 7 and the heavy chain variable region has the amino acid sequence of SEQ ID NO: 8;
- (e) a nucleic acid molecule encoding an antibody wherein the light chain variable region has the amino acid sequence of SEQ ID NO: 9 and the heavy chain variable region has the amino acid sequence of SEQ ID NO: 10;
- (f) a nucleic acid molecule encoding an antibody wherein the light chain variable region has the amino acid sequence of SEQ ID NO: 11 and the heavy chain variable region has the amino acid sequence of SEQ ID NO: 12;
- (g) a nucleic acid molecule encoding an antibody wherein the light chain variable region has the amino acid sequence of SEQ ID NO: 13 and the heavy chain variable region has the amino acid sequence of SEQ ID NO: 14;
- (h) a nucleic acid molecule encoding an antibody wherein the light chain variable region has the amino acid sequence of SEQ ID NO: 15 and the heavy chain variable region has the amino acid sequence of SEQ ID NO: 16; and
- (i) a nucleic acid molecule encoding an antibody wherein the light chain variable region has the amino acid sequence of SEQ ID NO: 17 and the heavy chain variable region has the amino acid sequence of SEQ ID NO: 18.

8. A nucleic acid molecule of claim 7 encoding an antibody comprising a heavy chain constant region having an amino acid sequence of SEQ ID NO: 25, SEQ ID NO: 26, or SEQ ID NO: 28.

9. A nucleic acid molecule of claim 7 encoding an antibody comprising a light chain constant region having the amino acid sequence of SEQ ID NO: 23.

10. A nucleic acid molecule of claim 7 encoding an antibody comprising a heavy chain constant region having an amino acid sequence of SEQ ID NO: 25, SEQ ID NO: 26, or SEQ ID NO: 28; and a light chain constant region having the amino acid sequence of SEQ ID NO: 23.

11. A nucleic acid molecule of claim 7 encoding an antibody comprising a light chain variable region having the amino acid sequence of SEQ ID NO: 3 and a heavy chain variable region having the amino acid sequence of SEQ ID NO: 4.

12. A nucleic acid molecule of claim 11 encoding an antibody comprising a heavy chain constant region having the amino acid sequence of SEQ ID NO: 28.

13. A nucleic acid molecule of claim 11 encoding an antibody comprising a light chain constant region having the amino acid sequence of SEQ ID NO: 23.

14. A nucleic acid molecule of claim 11 encoding an antibody comprising a heavy chain constant region having the amino acid sequence of SEQ ID NO: 28 and a light chain constant region having the amino acid sequence of SEQ ID NO: 23.

15. A nucleic acid molecule encoding a humanized antibody that binds to P-selectin wherein the antibody comprises a light chain variable region having an amino acid sequence selected from the group consisting of: SEQ ID NO: 1; SEQ ID NO: 3; SEQ ID NO: 5; SEQ ID NO: 7; SEQ ID NO: 9; SEQ ID NO: 11; SEQ ID NO: 13; SEQ ID NO: 15; SEQ ID NO: 17; SEQ ID NO: 19; and SEQ ID NO: 21; or a heavy chain variable region having an amino acid sequence selected from the group consisting of: SEQ ID NO: 2; SEQ ID NO: 4; SEQ ID NO: 6; SEQ ID NO: 8; SEQ ID NO: 10; SEQ ID NO: 12; SEQ ID NO: 14; SEQ ID NO: 16; SEQ ID NO: 18; SEQ ID NO: 20; and SEQ ID NO: 22.

16. A nucleic acid molecule of claim 15 encoding an antibody comprising a light chain variable region having the amino acid sequence of SEQ ID NO: 3.

17. A nucleic acid molecule of claim 15 encoding an antibody comprising a heavy chain variable region having the amino acid sequence of SEQ ID NO: 4.

18. A nucleic acid molecule encoding a humanized antibody that binds to P-selectin selected from the group consisting of:
- (a) a nucleic acid molecule encoding an antibody wherein the light chain variable region of the antibody comprises the amino acid sequences of the 3 complementarity determining regions in SEQ ID NO: 19; and the heavy chain variable region of the antibody comprises the amino acid sequences of the 3 complementarity determining regions in SEQ ID NO: 20; and
- (b) a nucleic acid molecule encoding an antibody wherein the light chain variable region of the antibody comprises the amino acid sequences of the 3 complementarity determining regions in SEQ ID NO: 21; and the heavy chain variable region of the antibody comprises the amino acid sequences of the 3 complementarity determining regions in SEQ ID NO: 22.

19. A nucleic acid molecule of claim 18 encoding an antibody comprising a light chain variable region comprising the 3 complementarity determining regions in SEQ ID NO: 19; and a heavy chain variable region comprising the 3 complementarity determining regions in SEQ ID NO: 20.

20. A nucleic acid molecule of claim 18 encoding an antibody comprising a light chain variable region comprising the 3 complementarity determining regions in SEQ ID NO: 21; and a heavy chain variable region comprising the 3 complementarity determining regions in SEQ ID NO: 22.

21. A nucleic acid molecule of claim 1 encoding an antibody comprising a light chain variable region comprising 3 complementarity determining regions having the amino acid sequences of: SEQ ID NO: 43 for CDR1, SEQ ID NO: 45 for CDR2, and SEQ ID NO: 47 for CDR3; and a heavy chain variable region comprising 3 complementarity determining regions having the amino acid sequences of: SEQ ID NO: 29 for CDR1, SEQ ID NO: 33 for CDR2, and SEQ ID NO: 38 for CDR3.

22. A nucleic acid molecule of claim 1 encoding an antibody comprising a light chain variable region comprising 3 complementarity determining regions having the amino acid sequences of: SEQ ID NO: 44 for CDR1, SEQ ID NO: 46 for CDR2, and SEQ ID NO: 49 for CDR3; and a heavy chain variable region comprising 3 complementarity determining regions having the amino acid sequences of: SEQ ID NO: 31 for CDR1, SEQ ID NO: 35 for CDR2, and SEQ ID NO: 40 for CDR3.

23. A nucleic acid molecule of claim 1 encoding an antibody comprising a light chain variable region comprising 3 complementarity determining regions having the amino acid sequences of: SEQ ID NO: 44 for CDR1, SEQ ID NO: 46 for CDR2, and SEQ ID NO: 49 for CDR3; and a heavy chain variable region comprising 3 complementarity determining regions having the amino acid sequences of: SEQ ID NO: 32 for CDR1, SEQ ID NO: 36 for CDR2, and SEQ ID NO: 41 for CDR3.

24. A nucleic acid molecule of claim 1 encoding an antibody comprising a light chain variable region comprising 3 complementarity determining regions having the amino acid sequences of: SEQ ID NO: 43 for CDR1, SEQ ID NO: 45 for CDR2, and SEQ ID NO: 50 for CDR3; and a heavy chain variable region comprising 3 complementarity determining regions having the amino acid sequences of: SEQ ID NO: 32 for CDR1, SEQ ID NO: 36 for CDR2, and SEQ ID NO: 41 for CDR3.

25. A nucleic acid molecule of claim 1 encoding an antibody comprising a light chain variable region comprising 3 complementarity determining regions having the amino acid sequences of: SEQ ID NO: 43 for CDR1, SEQ ID NO: 45 for CDR2, and SEQ ID NO: 50 for CDR3; and a heavy chain variable region comprising 3 complementarity determining regions having the amino acid sequences of: SEQ ID NO: 31 for CDR1, SEQ ID NO: 35 for CDR2, and SEQ ID NO: 40 for CDR3.

26. A nucleic acid molecule of claim 1 encoding an antibody comprising a light chain variable region comprising 3 complementarity determining regions having the amino acid sequences of: SEQ ID NO: 44 for CDR1, SEQ ID NO: 46 for CDR2, and SEQ ID NO: 51 for CDR3; and a heavy chain variable region comprising 3 complementarity determining regions having the amino acid sequences of: SEQ ID NO: 29 for CDR1, SEQ ID NO: 37 for CDR2, and SEQ ID NO: 42 for CDR3.

27. A nucleic acid molecule of claim 1 encoding an antibody comprising a light chain variable region comprising 3 complementarity determining regions having the amino acid sequences of: SEQ ID NO: 44 for CDR1, SEQ ID NO: 46 for CDR2, and SEQ ID NO: 51 for CDR3; and a heavy chain variable region comprising 3 complementarity determining regions having the amino acid sequences of: SEQ ID NO: 29 for CDR1, SEQ ID NO: 37 for CDR2, and SEQ ID NO: 42 for CDR3.

28. A nucleic acid molecule of claim 1 encoding an antibody comprising a light chain variable region comprising 3 complementarity determining regions having the amino acid sequences of: SEQ ID NO: 43 for CDR1, SEQ ID NO: 45 for CDR2, and SEQ ID NO: 52 for CDR3; and a heavy chain variable region comprising 3 complementarity determining regions having the amino acid sequences of: SEQ ID NO: 29 for CDR1, SEQ ID NO: 37 for CDR2, and SEQ ID NO: 42 for CDR3.

29. A vector comprising a nucleic acid molecule of claim 1.
30. A host cell comprising a vector of claim 29.
31. A vector comprising a nucleic acid molecule of claim 3.
32. A host cell comprising a vector of claim 31.
33. A vector comprising a nucleic acid molecule of claim 4.
34. A host cell comprising a vector of claim 33.
35. A vector comprising a nucleic acid molecule of claim 11.
36. A host cell comprising a vector of claim 35.
37. A vector comprising a nucleic acid molecule of claim 14.
38. A host cell comprising a vector of claim 37.
39. A vector comprising a nucleic acid molecule of claim 16.
40. A host cell comprising a vector of claim 39.
41. A vector comprising a nucleic acid molecule of claim 17.
42. A host cell comprising a vector of claim 41.

* * * * *

UNITED STATES PATENT AND TRADEMARK OFFICE
CERTIFICATE OF CORRECTION

| | | |
|---|---|---|
| PATENT NO. | : 7,754,867 B2 | Page 1 of 1 |
| APPLICATION NO. | : 12/481623 | |
| DATED | : July 13, 2010 | |
| INVENTOR(S) | : Yvo Graus et al. | |

It is certified that error appears in the above-identified patent and that said Letters Patent is hereby corrected as shown below:

Claim 1, column 77, line 14, after "humanized", insert -- or human --

Claim 15, column 80, line 4, after "humanized", insert -- or human --

Claim 18, column 80, line 22, after "humanized", insert -- or human --

Signed and Sealed this
Eighteenth Day of October, 2011

David J. Kappos
*Director of the United States Patent and Trademark Office*

SEQUENCE LISTING

```
<160> NUMBER OF SEQ ID NOS: 57

<210> SEQ ID NO 1
<211> LENGTH: 107
<212> TYPE: PRT
<213> ORGANISM: Homo sapiens

<400> SEQUENCE: 1

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asn Asn Trp Pro Leu
                85                  90                  95

Thr Phe Gly Gly Gly Thr Lys Val Glu Ile Lys
```

```
                    100                 105

<210> SEQ ID NO 2
<211> LENGTH: 124
<212> TYPE: PRT
<213> ORGANISM: Homo sapiens

<400> SEQUENCE: 2

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Gly Ile Thr Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Gly Arg Ile Ser Met Asp Arg Gly Val Lys Asn Asn Trp Phe Asp
            100                 105                 110

Pro Trp Gly Gln Gly Thr Leu Val Thr Val Ser Ser
        115                 120

<210> SEQ ID NO 3
<211> LENGTH: 107
<212> TYPE: PRT
<213> ORGANISM: Homo sapiens

<400> SEQUENCE: 3

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 4
<211> LENGTH: 124
<212> TYPE: PRT
<213> ORGANISM: Homo sapiens

<400> SEQUENCE: 4

Glu Val Gln Leu Val Glu Ser Gly Gly Gly Leu Val Arg Pro Gly Gly
 1               5                  10                  15

Ser Leu Arg Leu Ser Cys Ala Ala Ser Gly Phe Thr Phe Ser Asn Tyr
            20                  25                  30

Asp Met His Trp Val Arg Gln Ala Thr Gly Lys Gly Leu Glu Trp Val
        35                  40                  45
```

```
Ser Ala Ile Thr Ala Ala Gly Asp Ile Tyr Tyr Pro Gly Ser Val Lys
            50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                 85                  90                  95

Arg Gly Arg Tyr Ser Gly Ser Ser Tyr Tyr Asn Asp Trp Phe Asp
            100                 105                 110

Pro Trp Gly Gln Gly Thr Leu Val Thr Val Ser Ser
            115                 120
```

<210> SEQ ID NO 5
<211> LENGTH: 107
<212> TYPE: PRT
<213> ORGANISM: Homo sapiens

<400> SEQUENCE: 5

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Glu Lys Ala Pro Lys Ser Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr His Ser Tyr Pro Leu
                 85                  90                  95

Thr Phe Gly Gly Gly Thr Lys Val Glu Ile Lys
            100                 105
```

<210> SEQ ID NO 6
<211> LENGTH: 128
<212> TYPE: PRT
<213> ORGANISM: Homo sapiens

<400> SEQUENCE: 6

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Glu Gly Leu Glu Trp Val
             35                  40                  45

Ala Val Ile Trp Tyr Asp Gly Thr Phe Lys Tyr Tyr Ala Asp Ser Val
 50                  55                  60

Lys Gly Arg Phe Thr Ile Ser Arg Asp Asn Lys Asn Thr Leu Ser
 65                  70                  75                  80

Leu Leu Met Asn Ser Leu Arg Ala Glu Asp Thr Ala Val Tyr Tyr Cys
                 85                  90                  95

Thr Arg Gly Gly Tyr Tyr Gly Ser Gly Ser Ser Phe Asp Tyr Tyr Tyr
            100                 105                 110

Tyr Gly Met Asp Val Trp Gly Gln Gly Thr Thr Val Thr Val Ser Ser
            115                 120                 125
```

<210> SEQ ID NO 7

```
<211> LENGTH: 107
<212> TYPE: PRT
<213> ORGANISM: Homo sapiens

<400> SEQUENCE: 7

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Glu Lys Ala Pro Lys Ser Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr His Ser Tyr Pro Leu
                 85                  90                  95

Thr Phe Gly Gly Gly Thr Lys Val Glu Ile Lys
            100                 105

<210> SEQ ID NO 8
<211> LENGTH: 117
<212> TYPE: PRT
<213> ORGANISM: Homo sapiens

<400> SEQUENCE: 8

Gln Val Gln Leu Val Gln Ser Gly Ala Glu Val Lys Lys Pro Gly Ala
  1               5                  10                  15

Ser Val Lys Val Ser Cys Lys Val Ser Gly Tyr Thr Leu Thr Glu Leu
             20                  25                  30

Ser Met His Trp Val Arg Gln Ala Pro Gly Lys Gly Leu Glu Trp Met
         35                  40                  45

Gly Gly Phe Asp Pro Glu Asp Gly Glu Thr Ile Tyr Ala Gln Lys Phe
 50                  55                  60

Gln Gly Arg Val Thr Met Thr Glu Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Asp Asp Leu Asp Tyr Phe Asp Tyr Trp Gly Gln Gly Thr Gln
            100                 105                 110

Val Thr Val Ser Ser
        115

<210> SEQ ID NO 9
<211> LENGTH: 108
<212> TYPE: PRT
<213> ORGANISM: Homo sapiens

<400> SEQUENCE: 9

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
 50                  55                  60
```

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Val Thr Phe Gly Gln Gly Thr Arg Leu Glu Ile Lys
            100                 105

<210> SEQ ID NO 10
<211> LENGTH: 117
<212> TYPE: PRT
<213> ORGANISM: Homo sapiens

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
                20                  25                  30

Ser Met His Trp Val Arg Gln Ala Pro Gly Lys Gly Leu Glu Trp Met
            35                  40                  45

Gly Gly Phe Asp Pro Glu Asp Gly Glu Thr Ile Tyr Ala Gln Lys Phe
        50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Asp Leu Asp Tyr Phe Asp Tyr Trp Gly Gln Gly Thr Gln
            100                 105                 110

Val Thr Val Ser Ser
        115

<210> SEQ ID NO 11
<211> LENGTH: 108
<212> TYPE: PRT
<213> ORGANISM: Homo sapiens

<400> SEQUENCE: 11

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Val Thr Phe Gly Gln Gly Thr Arg Leu Glu Ile Lys
            100                 105

<210> SEQ ID NO 12
<211> LENGTH: 128
<212> TYPE: PRT
<213> ORGANISM: Homo sapiens

<400> SEQUENCE: 12

Gln Val Gln Leu Val Glu Ser Gly Gly Gly Val Val Gln Pro Gly Arg

```
                1               5                  10                 15
Ser Leu Arg Leu Ser Cys Ala Ala Ser Gly Phe Thr Phe Ser Ser Tyr
                    20                  25                  30

Gly Met His Trp Val Arg Gln Ala Pro Gly Glu Gly Leu Glu Trp Val
            35                  40                  45

Ala Val Ile Trp Tyr Asp Gly Thr Phe Lys Tyr Tyr Ala Asp Ser Val
        50                  55                  60

Lys Gly Arg Phe Thr Ile Ser Arg Asp Asn Ser Lys Asn Thr Leu Ser
 65                 70                  75                  80

Leu Leu Met Asn Ser Leu Arg Ala Glu Asp Thr Ala Val Tyr Tyr Cys
                85                  90                  95

Thr Arg Gly Gly Tyr Tyr Gly Ser Gly Ser Ser Phe Asp Tyr Tyr Tyr
                    100                 105                 110

Tyr Gly Met Asp Val Trp Gly Gln Gly Thr Thr Val Thr Val Ser Ser
            115                 120                 125
```

<210> SEQ ID NO 13
<211> LENGTH: 107
<212> TYPE: PRT
<213> ORGANISM: Homo sapiens

<400> SEQUENCE: 13

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                 70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105
```

<210> SEQ ID NO 14
<211> LENGTH: 124
<212> TYPE: PRT
<213> ORGANISM: Homo sapiens

<400> SEQUENCE: 14

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Asp Met His Trp Val Arg Gln Ala Thr Gly Lys Gly Leu Glu Trp Val
            35                  40                  45

Ser Ala Ile Ser Thr Ala Gly Asp Thr Tyr Tyr Pro Gly Ser Val Lys
        50                  55                  60

Gly Arg Phe Thr Ile Ser Arg Glu Asn Ala Lys Asn Ser Leu Tyr Leu
 65                 70                  75                  80

Gln Met Asn Ser Leu Arg Val Gly Asp Thr Ala Val Tyr Tyr Cys Ala
                85                  90                  95

Arg Gly Arg Phe Asp Gly Ser Gly Ser Tyr Tyr Asn Asp Trp Phe Asp
```

```
                   100                 105                 110

Pro Trp Gly Gln Gly Thr Leu Val Thr Val Ser Ser
        115                 120

<210> SEQ ID NO 15
<211> LENGTH: 107
<212> TYPE: PRT
<213> ORGANISM: Homo sapiens

<400> SEQUENCE: 15

Ala Ile Gln Leu Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Glu Lys Ala Pro Lys Ser Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Leu
                 85                  90                  95

Thr Phe Gly Gly Gly Thr Lys Val Glu Ile Lys
            100                 105

<210> SEQ ID NO 16
<211> LENGTH: 124
<212> TYPE: PRT
<213> ORGANISM: Homo sapiens

<400> SEQUENCE: 16

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Asp Met His Trp Val Arg Gln Ala Thr Gly Lys Gly Leu Glu Trp Val
         35                  40                  45

Ser Ala Ile Ser Thr Ala Gly Asp Thr Tyr Tyr Pro Gly Ser Val Lys
     50                  55                  60

Gly Arg Phe Thr Ile Ser Arg Glu Asn Ala Lys Asn Ser Leu Tyr Leu
 65                  70                  75                  80

Gln Met Asn Ser Leu Arg Val Gly Asp Thr Ala Val Tyr Tyr Cys Ala
                 85                  90                  95

Arg Gly Arg Phe Asp Gly Ser Gly Ser Tyr Tyr Asn Asp Trp Phe Asp
            100                 105                 110

Pro Trp Gly Gln Gly Thr Leu Val Thr Val Ser Ser
        115                 120

<210> SEQ ID NO 17
<211> LENGTH: 107
<212> TYPE: PRT
<213> ORGANISM: Homo sapiens

<400> SEQUENCE: 17

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
             20                  25                  30
```

```
Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Tyr Asn Trp Pro Leu
                 85                  90                  95

Thr Phe Gly Gly Gly Thr Lys Val Glu Ile Lys
                100                 105

<210> SEQ ID NO 18
<211> LENGTH: 124
<212> TYPE: PRT
<213> ORGANISM: Homo sapiens

<400> SEQUENCE: 18

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Asp Met His Trp Val Arg Gln Ala Thr Gly Lys Gly Leu Glu Trp Val
         35                  40                  45

Ser Ala Ile Ser Thr Ala Gly Asp Thr Tyr Tyr Pro Gly Ser Val Lys
 50                  55                  60

Gly Arg Phe Thr Ile Ser Arg Glu Asn Ala Lys Asn Ser Leu Tyr Leu
 65                  70                  75                  80

Gln Met Asn Ser Leu Arg Val Gly Asp Thr Ala Val Tyr Tyr Cys Ala
                 85                  90                  95

Arg Gly Arg Phe Asp Gly Ser Gly Ser Tyr Tyr Asn Asp Trp Phe Asp
            100                 105                 110

Pro Trp Gly Gln Gly Thr Leu Val Thr Val Ser Ser
            115                 120

<210> SEQ ID NO 19
<211> LENGTH: 108
<212> TYPE: PRT
<213> ORGANISM: Homo sapiens

<400> SEQUENCE: 19

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Phe Thr Phe Gly Pro Gly Thr Lys Val Asp Ile Lys
                100                 105

<210> SEQ ID NO 20
```

```
<211> LENGTH: 119
<212> TYPE: PRT
<213> ORGANISM: Homo sapiens

<400> SEQUENCE: 20

Gln Val Gln Leu Val Glu Ser Gly Gly Val Val Gln Pro Gly Arg
 1               5                  10                  15

Ser Leu Arg Leu Ser Cys Ala Ala Thr Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Lys Tyr Tyr Thr Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Asn Trp Ile Asp Val Phe Asp Ile Trp Gly Gln Gly
            100                 105                 110

Thr Met Val Thr Val Ser Ser
        115

<210> SEQ ID NO 21
<211> LENGTH: 107
<212> TYPE: PRT
<213> ORGANISM: Homo sapiens

<400> SEQUENCE: 21

Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Ala
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys
            100                 105

<210> SEQ ID NO 22
<211> LENGTH: 124
<212> TYPE: PRT
<213> ORGANISM: Homo sapiens

<400> SEQUENCE: 22

Gln Pro Gln Leu Val Gln Ser Gly Ala Glu Val Lys Lys Pro Gly Ala
 1               5                  10                  15

Ser Val Lys Val Ser Cys Lys Val Ser Gly Asn Thr Leu Thr Glu Leu
                20                  25                  30

Ser Met His Trp Val Arg Gln Ala Pro Gly Lys Gly Leu Glu Trp Met
            35                  40                  45

Gly Gly Phe Asp Pro Glu Asn Gly Glu Ala Ile Tyr Ala Gln Lys Phe
        50                  55                  60
```

```
Gln Gly Arg Val Thr Met Thr Ala Asp Thr Ser Thr Asp Thr Ala Tyr
 65                  70                  75                  80

Met Asp Leu Ser Ser Leu Arg Ser Glu Asp Thr Ala Val Tyr Tyr Cys
                 85                  90                  95

Ala Thr Asp Leu Ala Gly Gly Ser Asp Phe Tyr Tyr Tyr Gly Leu Asp
            100                 105                 110

Val Trp Gly Gln Gly Thr Thr Val Thr Val Ser Ser
        115                 120
```

<210> SEQ ID NO 23
<211> LENGTH: 107
<212> TYPE: PRT
<213> ORGANISM: Homo sapiens

<400> SEQUENCE: 23

```
Arg Thr Val Ala Ala Pro Ser Val Phe Ile Phe Pro Pro Ser Asp Glu
  1               5                  10                  15

Gln Leu Lys Ser Gly Thr Ala Ser Val Val Cys Leu Leu Asn Asn Phe
                 20                  25                  30

Tyr Pro Arg Glu Ala Lys Val Gln Trp Lys Val Asp Asn Ala Leu Gln
             35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 24
<211> LENGTH: 330
<212> TYPE: PRT
<213> ORGANISM: Homo sapiens

<400> SEQUENCE: 24

```
Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 25
<211> LENGTH: 329
<212> TYPE: PRT
<213> ORGANISM: Homo sapiens

<400> SEQUENCE: 25

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205
```

```
Gly Leu Pro Ser Ser Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325
```

<210> SEQ ID NO 26
<211> LENGTH: 330
<212> TYPE: PRT
<213> ORGANISM: Homo sapiens

<400> SEQUENCE: 26

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
```

```
                    245                 250                 255
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 27
<211> LENGTH: 327
<212> TYPE: PRT
<213> ORGANISM: Homo sapiens

<400> SEQUENCE: 27

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285
```

```
Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 28
<211> LENGTH: 327
<212> TYPE: PRT
<213> ORGANISM: Homo sapiens

<400> SEQUENCE: 28

Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
            325
```

<210> SEQ ID NO 29
<211> LENGTH: 5
<212> TYPE: PRT
<213> ORGANISM: Homo sapiens

<400> SEQUENCE: 29

Ser Tyr Asp Met His
1               5

<210> SEQ ID NO 30
<211> LENGTH: 5
<212> TYPE: PRT
<213> ORGANISM: Homo sapiens

<400> SEQUENCE: 30

Asn Tyr Asp Met His
1               5

<210> SEQ ID NO 31
<211> LENGTH: 5
<212> TYPE: PRT
<213> ORGANISM: Homo sapiens

<400> SEQUENCE: 31

Ser Tyr Gly Met His
1               5

<210> SEQ ID NO 32
<211> LENGTH: 5
<212> TYPE: PRT
<213> ORGANISM: Homo sapiens

<400> SEQUENCE: 32

Glu Leu Ser Met His
1               5

<210> SEQ ID NO 33
<211> LENGTH: 16
<212> TYPE: PRT
<213> ORGANISM: Homo sapiens

<400> SEQUENCE: 33

Gly Ile Thr Thr Ala Gly Asp Thr Tyr Tyr Pro Gly Ser Val Lys Gly
1               5                   10                  15

<210> SEQ ID NO 34
<211> LENGTH: 16
<212> TYPE: PRT
<213> ORGANISM: Homo sapiens

<400> SEQUENCE: 34

Ala Ile Thr Ala Ala Gly Asp Ile Tyr Tyr Pro Gly Ser Val Lys Gly
1               5                   10                  15

<210> SEQ ID NO 35
<211> LENGTH: 17
<212> TYPE: PRT
<213> ORGANISM: Homo sapiens

<400> SEQUENCE: 35

Val Ile Trp Tyr Asp Gly Thr Phe Lys Tyr Tyr Ala Asp Ser Val Lys
1               5                   10                  15

Gly

<210> SEQ ID NO 36
<211> LENGTH: 17
<212> TYPE: PRT
<213> ORGANISM: Homo sapiens

<400> SEQUENCE: 36

Gly Phe Asp Pro Glu Asp Gly Glu Thr Ile Tyr Ala Gln Lys Phe Gln
 1               5                  10                  15

Gly

<210> SEQ ID NO 37
<211> LENGTH: 16
<212> TYPE: PRT
<213> ORGANISM: Homo sapiens

<400> SEQUENCE: 37

Ala Ile Ser Thr Ala Gly Asp Thr Tyr Tyr Pro Gly Ser Val Lys Gly
 1               5                  10                  15

<210> SEQ ID NO 38
<211> LENGTH: 16
<212> TYPE: PRT
<213> ORGANISM: Homo sapiens

<400> SEQUENCE: 38

Gly Arg Ile Ser Met Asp Arg Gly Val Lys Asn Asn Trp Phe Asp Pro
 1               5                  10                  15

<210> SEQ ID NO 39
<211> LENGTH: 16
<212> TYPE: PRT
<213> ORGANISM: Homo sapiens

<400> SEQUENCE: 39

Gly Arg Tyr Ser Gly Ser Gly Ser Tyr Tyr Asn Asp Trp Phe Asp Pro
 1               5                  10                  15

<210> SEQ ID NO 40
<211> LENGTH: 19
<212> TYPE: PRT
<213> ORGANISM: Homo sapiens

<400> SEQUENCE: 40

Gly Gly Tyr Tyr Gly Ser Gly Ser Ser Phe Asp Tyr Tyr Tyr Tyr Gly
 1               5                  10                  15

Met Asp Val

<210> SEQ ID NO 41
<211> LENGTH: 8
<212> TYPE: PRT
<213> ORGANISM: Homo sapiens

<400> SEQUENCE: 41

Asp Asp Leu Asp Tyr Phe Asp Tyr
 1               5

<210> SEQ ID NO 42
<211> LENGTH: 16
<212> TYPE: PRT
<213> ORGANISM: Homo sapiens

<400> SEQUENCE: 42

-continued

Gly Arg Phe Asp Gly Ser Gly Ser Tyr Tyr Asn Asp Trp Phe Asp Pro
1               5                   10                  15

<210> SEQ ID NO 43
<211> LENGTH: 11
<212> TYPE: PRT
<213> ORGANISM: Homo sapiens

<400> SEQUENCE: 43

Arg Ala Ser Gln Ser Val Ser Ser Tyr Leu Ala
1               5                   10

<210> SEQ ID NO 44
<211> LENGTH: 11
<212> TYPE: PRT
<213> ORGANISM: Homo sapiens

<400> SEQUENCE: 44

Arg Ala Ser Gln Gly Ile Ser Ser Trp Leu Ala
1               5                   10

<210> SEQ ID NO 45
<211> LENGTH: 7
<212> TYPE: PRT
<213> ORGANISM: Homo sapiens

<400> SEQUENCE: 45

Asp Ala Ser Asn Arg Ala Thr
1               5

<210> SEQ ID NO 46
<211> LENGTH: 7
<212> TYPE: PRT
<213> ORGANISM: Homo sapiens

<400> SEQUENCE: 46

Ala Ala Ser Ser Leu Gln Ser
1               5

<210> SEQ ID NO 47
<211> LENGTH: 9
<212> TYPE: PRT
<213> ORGANISM: Homo sapiens

<400> SEQUENCE: 47

Gln Gln Arg Asn Asn Trp Pro Leu Thr
1               5

<210> SEQ ID NO 48
<211> LENGTH: 9
<212> TYPE: PRT
<213> ORGANISM: Homo sapiens

<400> SEQUENCE: 48

Gln Gln Arg Ser Asn Trp Pro Leu Thr
1               5

<210> SEQ ID NO 49
<211> LENGTH: 9
<212> TYPE: PRT
<213> ORGANISM: Homo sapiens

<400> SEQUENCE: 49

Gln Gln Tyr His Ser Tyr Pro Leu Thr
1               5

<210> SEQ ID NO 50
<211> LENGTH: 10
<212> TYPE: PRT
<213> ORGANISM: Homo sapiens

<400> SEQUENCE: 50

Gln Gln Arg Ser Asn Trp Pro Pro Val Thr
 1               5                  10

<210> SEQ ID NO 51
<211> LENGTH: 9
<212> TYPE: PRT
<213> ORGANISM: Homo sapiens

<400> SEQUENCE: 51

Gln Gln Tyr Asn Ser Tyr Pro Leu Thr
 1               5

<210> SEQ ID NO 52
<211> LENGTH: 9
<212> TYPE: PRT
<213> ORGANISM: Homo sapiens

<400> SEQUENCE: 52

Gln Gln Arg Tyr Asn Trp Pro Leu Thr
 1               5

<210> SEQ ID NO 53
<211> LENGTH: 4
<212> TYPE: PRT
<213> ORGANISM: Homo sapiens

<400> SEQUENCE: 53

Glu Leu Leu Gly
 1

<210> SEQ ID NO 54
<211> LENGTH: 5
<212> TYPE: PRT
<213> ORGANISM: Homo sapiens

<400> SEQUENCE: 54

Ala Leu Pro Ala Pro
 1               5

<210> SEQ ID NO 55
<211> LENGTH: 5
<212> TYPE: PRT
<213> ORGANISM: Homo sapiens

<400> SEQUENCE: 55

Gly Leu Pro Ser Ser
 1               5

<210> SEQ ID NO 56
<211> LENGTH: 4
<212> TYPE: PRT
<213> ORGANISM: Homo sapiens

<400> SEQUENCE: 56

Glu Phe Leu Gly
 1

```
<210> SEQ ID NO 57
<211> LENGTH: 5
<212> TYPE: PRT
<213> ORGANISM: Homo sapiens

<400> SEQUENCE: 57

Gly Leu Pro Ala Pro
 1               5
```